(12) United States Patent
Gromeier et al.

(10) Patent No.: US 6,464,972 B1
(45) Date of Patent: Oct. 15, 2002

(54) RECOMBINANT POLIOVIRUS FOR THE TREATMENT OF CANCER

(75) Inventors: Matthias Gromeier, Stony Brook; Eckard Wimmer, East Setauket, both of NY (US)

(73) Assignee: The Research Foundation of State University of New York, Albany, NY (US)

(*) Notice: Subject to any disclaimer, the term of this patent is extended or adjusted under 35 U.S.C. 154(b) by 0 days.

(21) Appl. No.: 09/566,581

(22) Filed: May 8, 2000

Related U.S. Application Data

(62) Division of application No. 09/129,686, filed on Aug. 5, 1998, now Pat. No. 6,264,940.

(51) Int. Cl.$^7$ .......................... A01N 63/00; C12N 7/04
(52) U.S. Cl. ........................... 424/93.2; 435/236
(58) Field of Search ................. 435/236, 235.1, 435/69.3; 424/93.2, 93.6

(56) References Cited

U.S. PATENT DOCUMENTS 5,674,729 A   10/1997   Wimmer et al. ......... 435/235.1

OTHER PUBLICATIONS

Leibel, S.A. , et al., *Cancer*, 35:1551–1557 (1975).
Walker, M.D., et al., *J. Neurosurg.*, 49:333–343 (1978).
Chang, C.H., et al., *Cancer*, 52:997–1007 (1983).
Bloom, H.J.G., *Int. J. Radiat. Oncol. Biol. Phys.*, 8:1083–1087 (1982).
Choucair, A.K., et al., *J. Neurosurg.*, 65:654–658 (1986).
Miller, A.D., *Nature*, 357:455–460 (1992).
Martuza, R.L., et al., *Science*, 252:854–856 (1991).
Bischoff, J.R., *Science*, 274:373–376 (1996).
Wood, M.J.A. , et al., *Gene Therapy*, 1:283–29, (1994).
Markert, J.M. , et al., *Neurosurgery*, 32:597–603 (1993).
Mineta T. , et al., *Nature Medicine*, 1:938–943 (1995).
Andreansky, S. , et al., *Cancer Res.*,57:1502–1509 (1997).
Izquierdo, M. , et al., *Gene Therapy*, 2:66–69 (1995).
Chen, S.H. , et al., *PNAS*, USA, 91:3054–3057 (1994).
Kandel, E.R. and Schwartz, J.H., ed. *Principles of Neural Science*, Chapter 2, pp. 14–23 Elsevier/North, Holland, 1981.
Black, I., ed. *Cellular and Molecular Biology of Neuronal Development*, Chapter 2, pp. 29–47, Plenum Press, New York, 1984.
Bodian, D., *Diseases of the Nervous System*, Chapter 170 pp.2323–2339, McGraw Hill, New York.
Ren, R., , et al., *Cell*, 63:353–362 (1990).
Koike, S. , et al., *PNAS*, USA, 88:951–955 (1991).
Sabin & Boulger, *J. Biol. Stand.*, 1:115–118 (1973).
Minor, P.D., *Dev. Biol. Stand.*, 78:17–26 (1993).
Wimmer, E. , et al., *Ann. Rev. Gen.*,27:353–436 (1993).
Gromeier, M. , et al., *Proc. Natl. Acad. Sci. USA*, 93:2370–2375 (1996).
Omata, T.,et al., *J. Virol.*, 58:348–358 (1986).
WHO Technical Report Series No. 80 (1990).
Kawamura, N., et al., *J Virol.*, 63:1302–1309 (1989).
Fogh, J. , et al., *J. Natl. Cancer Inst.*, 59:221–226 (1997).
Agol , et al., *J. Virol.*, 63:4034–4038 (1989).
LaMonica, N. and Rancaniello, V.R., *J. Virol.*, 63:2357–2360 (1989).
M. Gromeier et al., *Vaccines*, 96: 19–25, 1996.
M. Gromeier et al., *PNAS*, 93: 2370–2375, 1996.
H. Lu et al., *PNAS*, 93: 1412–1417, 1996.
M. Gromeier et al.,*J. of Neurovirology*, vol. 3, No. suppl. 1: 35–38, 1997.
L. Alexander et al., *PNAS*, 91: 1406–1410, 1994.
A. Nomoto et al., *Vaccines*, 6:134–137, 1988.
R. Altmeyer et al., *Virology*, 184: 636–644, 1991.

*Primary Examiner*—Donna C. Wortman
(74) *Attorney, Agent, or Firm*—Scully, Scott, Murphy & Presser

(57) ABSTRACT

The present invention is directed to non-pathogenic, oncolytic, recombinant polioviruses for the treatment of various forms of malignant tumors. The recombinant polioviruses of the invention are those in which the internal ribosomal entry site (IRES) of the wild type poliovirus was exchanged with the IRES of other picornaviruses, and optionally P1, P3 or the 3'NTR thereof was exchanged with that of poliovirus Sabin type. More particularly, the present invention is directed to the administration of the non-pathogenic, oncolytic, recombinant poliovirus to the tumor directly, intrathecally or intravenously to cause tumor necrosis. The method of the present invention is particularly useful for the treatment of malignant tumors in various organs, such as: breast, colon, bronchial passage, epithelial lining of the gastrointestinal, upper respiratory and genitourinary tracts, liver, prostate and the brain. Astounding remissions in experimental animals have been demonstrated for the treatment of malignant glioblastoma multiforme, an almost universally fatal neoplasm of the central nervous system.

32 Claims, 22 Drawing Sheets

FIG. 3A

Neurovirulence testing in *Cynomolgus* monkeys*

| Monkey# | Virus strain tested | Lesion score | Clinical Obserevations |
|---|---|---|---|
| 1 | PV1 (RIPOS) | 0.60 | no paralysis |
| 2 | | 0.70 | no paralysis |
| 3 | | 0.62 | partial paralysis[a] |
| 4 | | 0.60 | partial paralysis[a] |
| 5 | PV1 (RIPO) | 0.70 | no paralysis |
| 6 | | 0.0 | no paralysis |
| 7 | | 0.40 | no paralysis |
| 8-12 | PV (S) | 0.92 | no or partial paralysis |
| 13-16 | PV1(M) | 2.48 | fatal poliomyelitis |

*Monkey neurovirulence assays were performed according to standardized procedured (WHO, 1983).

FIG. 3B

Neurovirulence staging of PV recombinants in CD155-tg mice

| | $LD_{50}(\log_{10}PFU)$* | | Intraspinal viral replication ($\log_{10}$PFU/mg tissue)[†] |
|---|---|---|---|
| | iv | ic | |
| PV1 (M) | 4.1 | 2.2 | |
| PV1 (S) | - | 6.3 | ND |
| PV1 (RIPOS) | - | - | |
| PV1 (RIPOS) | - | - | ND |
| | | | 0  1  2  3  4  5  6 |

* A negative sign indicates that poliomyelitic disease with fatal outcome was not observed after inoculation of $10^9$ PFU.

† Virus titers were determined from homogenized spinal cord tissue from PV-infected CD155-tg mice. Each bar represents the viral yield of a consecutive day p.i. starting with day one read from above.

key:

- PV1(M)
- PV/HRV2
- PV/HRV14
- PV/CB4
- PV/E9 hrs p.i.: hours post infection

FIG. 5

| Viral Construct | 5'NTR Structure | $LD_{50}^{ic}$ ($\log_{10}$PFU) |
|---|---|---|
| PV1(M) | | 2.2 |
| PV1(RIPO) | | - |
| PV1(RIPOS) | | - |
| PV1(R2-4) | | 3.0 |
| PV1(R2-4,6) | | - |
| PV1(R5) | | - |
| PV1(R2-5) | | - |
| PV1(R5-6) | | - |
| PV1(R6) | | - |

Stem-loops labeled (I), (II), (III), (IV), (V), (VI); ORF regions P1, P2, P3.

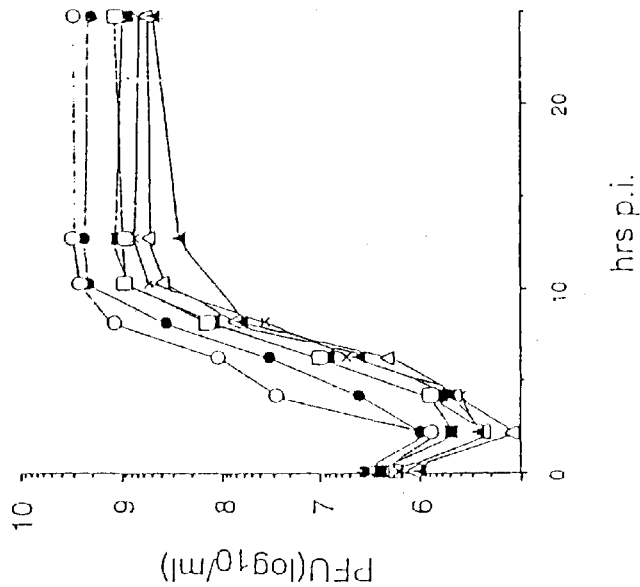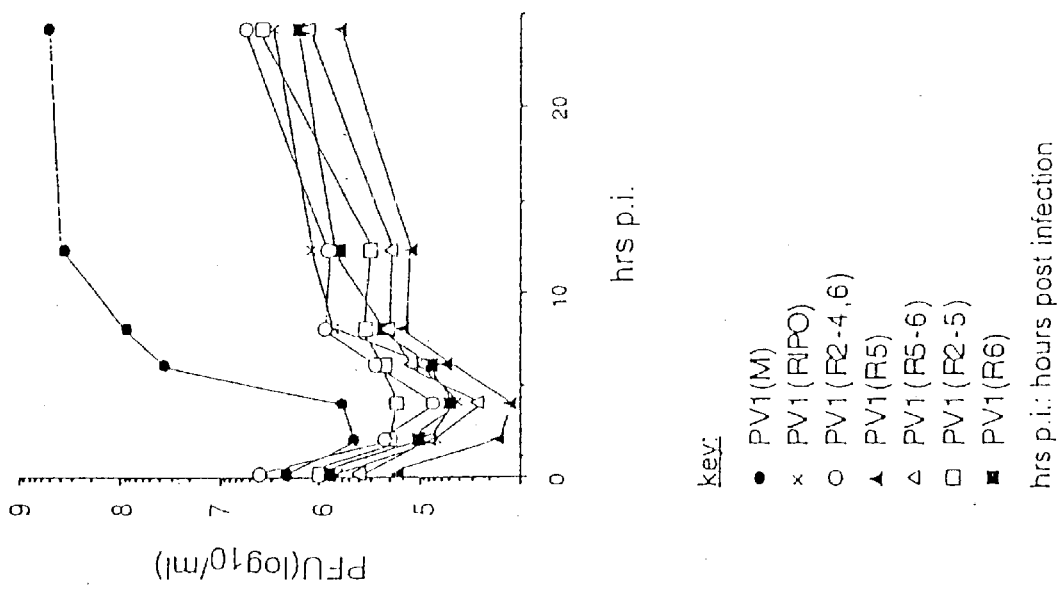

Fig. 7

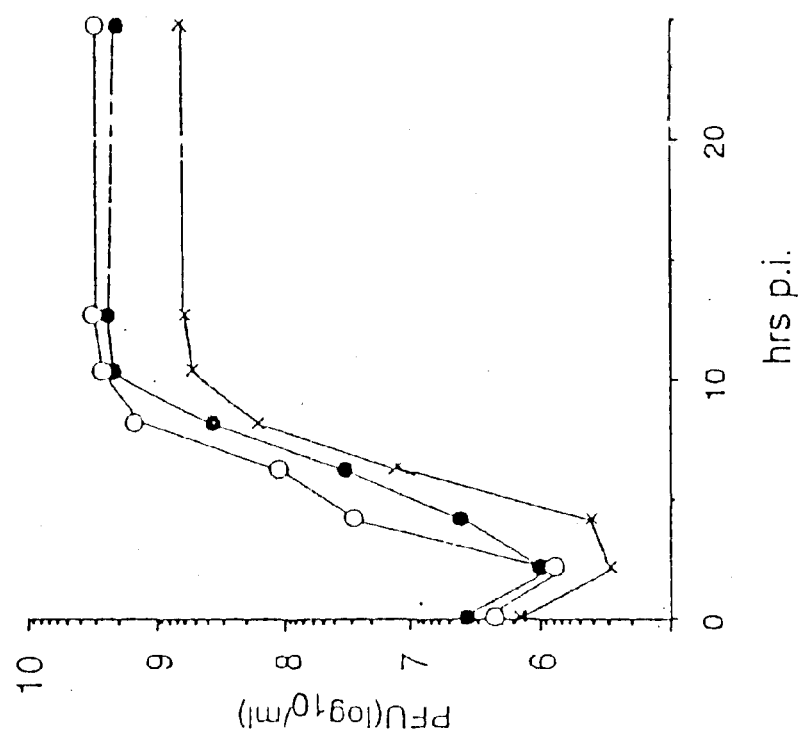
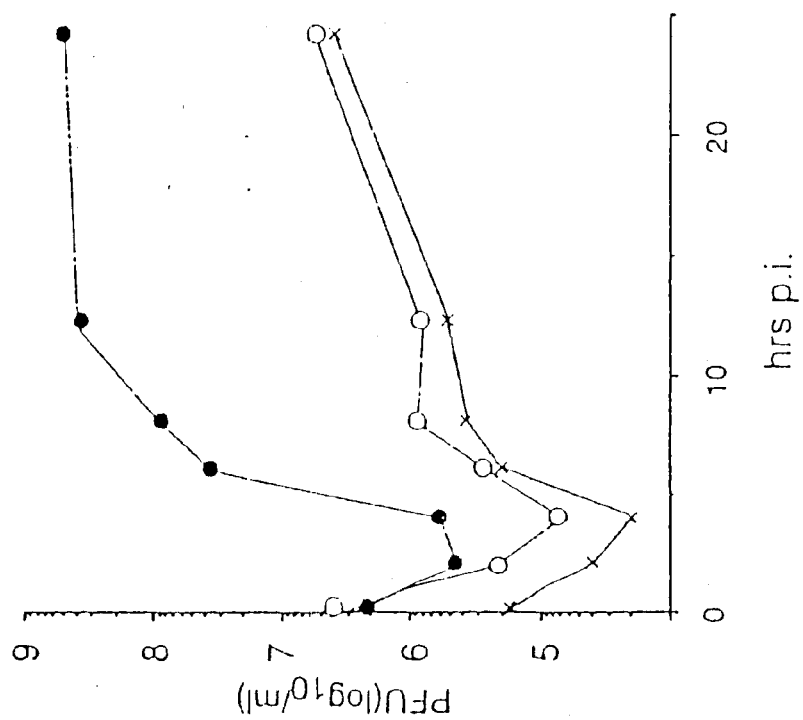

FIG. 8C

Neurovirulent indices of PV/HRV2 chimeras in CD155 tg mice.

| Virus strain | $LD_{50}^{iv}(log10pfu)^a$ | $LD_{50}^{ic}(log10pfu)^b$ |
|---|---|---|
| PV1 (M) | 4.0 | 2.2 |
| PV1 (RIPO) | -c | - |
| PV1 (prr) | -c | - | a  $LD_{50}^{iv}$=after intravenous administration of virus b  $LD_{50}^{ic}$=after intracerebral administration of virus c  a horizontal bar indicates that inoculation of 1x 10$^9$pfu of the virus variant in question did not lead to clinical symptoms Growth curves in glioma and neuronal cell lines key:

solid symbols= PV1(RIPO)
open symbols= wild-type PV1(Mahoney)
circles= glioblastoma HTB-14
triangles= glioblastoma HTB-15
squares= neuroblastoma SK-N-MC hrs p.i.: hours post infection Medulloblastoma:
HTB-185, medulloblastoma,
primary tumor Glioblastoma multiforme:
SF767, glioblastoma, primary tumor
SF763, glioblastoma, primary tumor
SF295, glioblastoma, primary tumor
SF188, glioblastoma, primary tumor Prostate carcinoma:
CRL-1435, prostate adenocarcinoma, metastatic, bone
HTB-81, prostate carcinoma, metastatic, brain Mammary carcinoma:
CRL-7721, mammary carcinoma, pleural effusion Hepatocellular carcinoma:
Hep-G2, hepatocellular carcinoma, primary tumor
HuH7, hepatocellular carcinoma, primary tumor Colorectal carcinoma:
CCL-230, colon adenocarcinoma, primary tumor Epidermoid carcinoma:
HEp-2, epidermoid carcinoma, larynx
HTB-32, epidermoid carcinoma, cervix Bronchial carcinoma:
CRL-2195, small cell lung carcinoma, primary tumor FIG. 18A
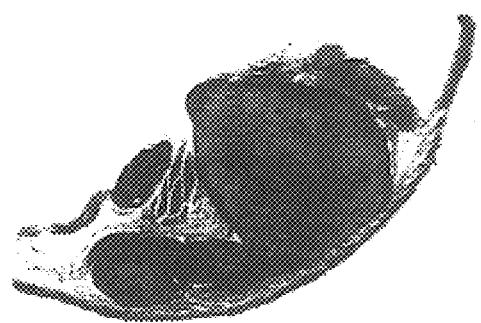
FIG. 18B
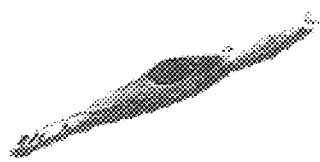
FIG. 18C
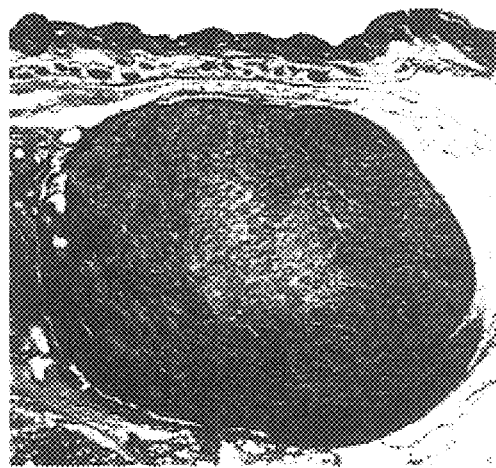

Kinetics of oncolysis by PV1(RIPO)

key:

solid squares= intraneoplastic replication
open squares= intracerebral replication
open circles= intrahepatic replication No virus
avg. survival 26 d.
treated/fatalities 6/6

$5 \times 10^7$ pfu PV1(RIPO) I.M.
avg. survival 39.6 d.
treated/fatalities 6/6

5x10⁷ pfu PV1(RIPO) I.V.
avg. survival 259 d.
prop. treated/fatalities 6/2

5x10⁷ pfu PV1(RIPO) I.C.
avg. survival ND.
prop. treated/fatalities 6/0

FIG. 22A
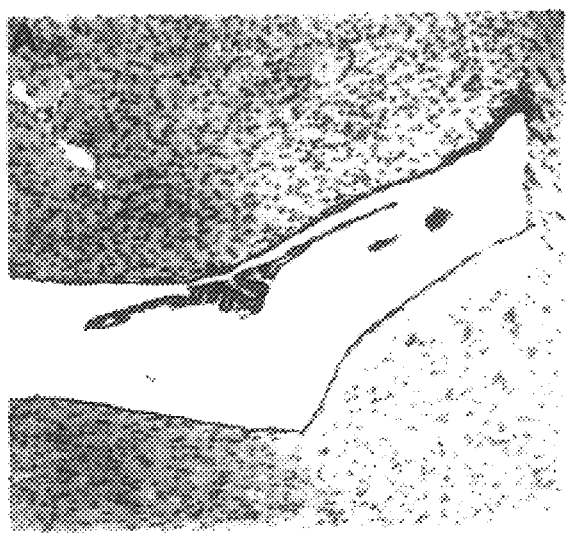
FIG. 22B
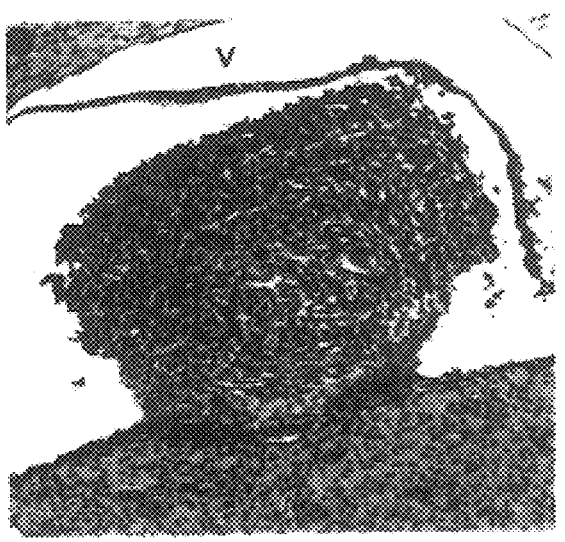
FIG. 22C
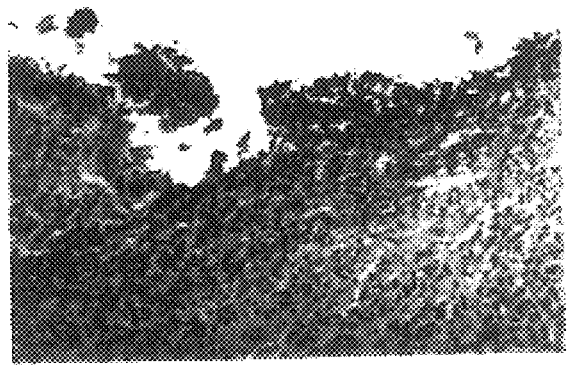

RECOMBINANT POLIOVIRUS FOR THE TREATMENT OF CANCER

This is a divisional of application Ser. No. 09/129,686 filed Aug. 5, 1998, now U.S. Pat. No. 6,264,490.

The present invention is directed to non-pathogenic, oncolytic, recombinant polioviruses for the treatment of various forms of malignant tumors. More particularly, the present invention is directed to the administration of the non-pathogenic, oncolytic, recombinant poliovirus to the tumor directly, intrathecally or intravenously to cause tumor necrosis. The method of the present invention is particularly useful for the treatment of malignant tumors in various organs, such as: breast, colon, bronchial passage, epithelial lining of the gastrointestinal, upper respiratory and genitourinary tracts, liver, prostate and the brain. Astounding remissions in experimental animals have been demonstrated for the treatment of malignant glioblastoma multiforme, an almost universally fatal neoplasm of the central nervous system.

The invention was made with Government support under No. AI32100-07 and AI39485 awarded by the National Institutes of Health. The government has certain rights in the invention.

BACKGROUND OF THE INVENTION

Known Methods of Treatment

It has been known that malignant tumors result from the uncontrolled growth of cells in an organ. The tumors grow to an extent where normal organ function may be critically impaired by tumor invasion, replacement of functioning tissue, competition for essential resources and, frequently, metastatic spread to secondary sites. Malignant cancer is the second leading cause of mortality in the United States.

Up to the present, the methods for treating malignant tumors include surgical resection, radiation and/or chemotherapy. However, numerous malignancies respond poorly to all traditionally available treatment options and there are serious adverse side effects to the known and practiced methods. There has been much advancement to reduce the severity of the side effects while increasing the efficiency of commonly practiced treatment regimens. However, many problems remain, and there is a need to search for alternative modalities of treatment. The search is particularly urgent for primary malignant tumors of the central nervous system. Brain tumors, especially glioblastomas, remain one of the most difficult therapeutic challenges. Despite the application of surgery, radiotherapy and chemotherapy, alone and in combination, glioblastomas are almost always fatal, with a median survival rate of less than a year and 5-year survival rates of 5.5% or less. None of the available therapeutic modes has substantially changed the relentless progress of glioblastomas.

Systematic studies of patients who were diagnosed with malignant glioma and underwent surgery to wholly or partially remove the tumor with subsequent chemotherapy and/or radiation showed that the survival rate after 1 year remains very low, particularly for patients who are over 60 years of age. Leibel, S. A., et al., *Cancer*, 35:1551–1557 (1975); Walker, M. D., et al., *J. Neurosurg.*, 49:333–343 (1978); Chang, C. H., et al., *Cancer*, 52:997–1007 (1983). Malignant gliomas have proven to be relatively resistant to radiation and chemotherapeutic regimens. Bloom, H. J. G., *Int. J. Radiat. Oncol. Biol. Phys.*, 8:1083–1087 (1982). Adding to the poor prognosis for malignant gliomas is the frequent tendency for local recurrence after surgical ablation and adjunct radiation/chemotherapy. Choucair, A. K., et al., *J. Neurosurg.*, 65:654–658 (1986).

Treatment of Cancer with Viruses

In recent years, there have been proposals to use viruses for the treatment of cancer: (1) as gene delivery vehicles, Miller, A. D., *Nature*, 357:455–460 (1992); (2) as direct oncolytic agents by using viruses that have been genetically modified to lose their pathogenic features, Martuza, R. L., et al., *Science*, 252:854–856 (1991); or (3) as agents to selectively damage malignant cells using viruses which have been genetic engineered for this purpose, Bischoff, J. R., et al., *Science*, 274:373–376 (1996).

Examples for the use of viruses against malignant gliomas include the following.

Herpes Simplex Virus dlsptk (HSVdlsptk), is a thymidine kinase (TK)-negative mutant of HSV. This virus is attenuated for neurovirulence because of a 360-base-pair deletion in the TK gene, the product of which is necessary for normal viral replication. It has been found that HSVdlsptk retains propagation potential in rapidly dividing malignant cells, causing cell lysis and death. Unfortunately, all defective herpes viruses with attenuated neuropathogenicity have been linked with serious symptoms of encephalitis in experimental animals. Wood, M. J. A., et al., *Gene Therapy*, 1:283–291 (1994). For example, in mice infected intracerebrally with HSVdlsptk, the $LD_{50}^{Ic}$ (intracranial administration) is $10^6$ pfu, a rather low dose. This limits the use of this mutant HSV. Markert, J. M., et al., *Neurosurgery*, 32:597–603 (1993). Other mutants of HSV have been proposed and tested. Nevertheless, death from viral encephalitis remains a problem. Mineta T., et al., *Nature Medicine*, 1:938–943 (1995); Andreansky, S., et al., *Cancer Res.*, 57:1502–1509 (1997).

Another proposal is to use retroviruses engineered to contain the HSV tk gene to express thymidine kinase which causes in vivo phosphorylation of nucleoside analogs, such as gancyclovir or acyclovir, blocking the replication of DNA and selectively killing the dividing cell. Izquierdo, M., et al., *Gene Therapy*, 2:66–69 (1995) reported the use of Moloney Murine Leukemia Virus (MoMLV) engineered with an insertion of the HSV tk gene with its own promoter. Follow-up of patients with glioblastomas that were treated with intraneoplastic inoculations of therapeutic retroviruses by MRI revealed shrinkage of tumors with no apparent short-term side effects. However, the experimental therapy had no effect on short-term or long-term survival of affected patients. Retroviral therapy is typically associated with the danger of serious long-term side effects (e.g. insertional mutagenesis).

Chen, S. H., et al., *PNAS*, USA, 91:3054–3057 (1994) reported the direct injection of a recombinant into experimentally induced gliomas in athymic mice. ADV/RSV-TK is an adenovirus containing the HSV-tk gene under transcriptional control of the rous sarcoma virus long terminal repeat, followed by treatment with gancyclovir. The treatment caused tumor necrosis without apparent involvement of the cellular immune response. The treated animals survived >50 days after tumor inoculation as contrasted with control tumor inoculated animals all of which died after 23 days. However, further long-term toxicity testing of neuronal, glial and endothelial cells is necessary to assess the potential of genetically engineered retroviruses for the treatment of cancers.

Recently, a novel strategy to use human pathogenic viruses for the treatment of malignant disease was introduced. Adenovirus engineered to selectively replicate within and destroy malignant cells expressing a modified p53 tumor suppressor offers an opportunity to target malignant cells without causing unwanted side effects due to virus propagation at extratumoral sites. Bischoff, J. R., et al., supra.

Similar systems have been developed to target malignancies of the upper airways, tumors that originate within the tissue naturally susceptible to adenovirus infection and that are easy accessible. However, Glioblastoma multiforme, highly malignant tumors composed out of widely heterogeneous cell types (hence the denomination multiforme) are characterized by exceedingly variable genotypes and are unlikely to respond to oncolytic virus systems directed against homogeneous tumors with uniform genetic abnormalities.

The Cells of the Central Nervous System

It is important to recognize that there are two classes of cells in the brain, the neural cells (neurons) and the neuroglia cells (glia). Neurons process information received from the peripheral receptors giving rise to perception and memory. Motor commands are issued and transmitted also by means of neurons to the various muscles of the body. There are nine times more glial cells than neurons. The glial cells have multiple functions. They serve as the supporting elements; segregate neurons into disparate groups and produce myelin. Based on physiological characteristics, there are five major classes of glial cells: astrocytes, oligodendrocytes, microglia, ependymal cells, and Schwann cells. Kandel, E. R. and Schwartz, J. H., ed., *Principles of Neural Science*, Chapter 2, pp. 14–23 Elsevier/North, Holland, 1981.

It is known that both the neurons and glial cells emerge from the neuroepithelium of the primitive neural tube. However, the timing and place of the mechanisms that underlie the separation of neuronal and glial cell lines have been unsettled and controversial. In 1889, His proposed that the germinative epithelium consists of two classes of precursor cells: one that produces neurons and another that produces glial cells. Although disputed, this has proven to be correct. It is believed that glial cells are generated after all or a majority of the neurons destined for a given structure have been formed. Black, I., ed. *Cellular and Molecular Biology of Neuronal Development*, Chapter 2, pp. 29–47, Plenum Press, New York, 1984.

The Poliovirus

Poliomyelitis is a disease of the central nervous system caused by infection with poliovirus. Poliovirus is a human enterovirus that belongs to the PIcornavIrIdae family and is classified into three stable serotypes. It is spherical, 20 nm in size, and contains a core of RNA coated with a capsule consisting of proteins. It is transmitted through the mucosa of the mouth, throat or the alimentary canal. All three poliovirus serotypes have been reported as causative agents of paralytic poliomyelitis, albeit at different frequencies (type 1>type 2>type 3).

However, infection by poliovirus does not necessarily lead to the development of poliomyelitis. On the contrary, the majority of infections (98–99%) lead to local gastrointestinal replication of the virus causing only mild symptoms, or no symptoms at all. Rarely does poliovirus invade the CNS where it selectively targets spinal cord anterior horn and medullary motor neurons for destruction. Bodian, D., in: *Diseases of the Nervous System*, Minckler, J. ed., McGraw-Hill, New York, pp.2323–2339 (1972).

The unusually restricted cell tropism of poliovirus leads to unique pathognomonic features. They are characterized by motor neuron loss in the spinal cord and the medulla, giving rise to the hallmark clinical sign of poliomyelitis, flaccid paralysis. Other neuronal components of the central nervous system as well as glial cells typically escape infection. In infected brain tissue under the electronmicroscope, severe changes are observed in motor neurons whereas no significant alterations are observed in the neuroglial components. Normal astrocyes and oligodendrocytes may be seen next to degenerate neurons or axons without evidence of infection or reaction. Bodian, D., supra. The restricted tropism of poliovirus is not understood. In addition to the restricted cell and tissue tropism, poliovirus only infects primates and primate cell cultures. Other mammalian species remain unaffected. Ren, R., et al., *Cell*, 63:353–362 (1990).

The isolation of poliovirus in 1908 led to intensive research efforts to understand the mechanisms of infection. The earlier work required the use of monkeys and chimpanzees as animal models. Such animals with longer life cycles are very costly and difficult to use in research. The discovery of the human poliovirus receptor (PVR) also known as CD155, the cellular docking molecule for poliovirus, led to the development of a transgenic mouse expressing the human poliovirus receptor as a new animal model for poliomyelitis. The pathogenicity of poliovirus may be studied using the transgenic mice. Ren et al. (1990); Koike, S., , et al., *PNAS*, USA, 88:951–955 (1991).

The early research efforts have also led to the development of attenuated PV strains that lack neuropathogenic potential and soon were tested as potential vaccine candidates for the prevention of poliomyelitis. The most effective of these are the Sabin strains of type 1, 2, and 3, of poliovirus developed by A. Sabin. Sabin & Boulger., *Dev. Biol. Stand.* 1:115–118 (1973). After oral administration of the live attenuated strains of poliovirus (the Sabin strains) vaccine-associated paralytic poliomyelitis has been observed in extremely rare cases. The occurrence of vaccine-associated paralytic polio has been correlated with the emergence of neurovirulent variants of the attenuated Sabin strains after immunization. Minor, P. D., *Dev. Biol. Stand.*, 78:17–26 (1993).

In order to understand the invention, it is important also to have an understanding of the structure of poliovirus.

All picornaviruses including enteroviruses, cardioviruses, rhinoviruses, aphthoviruses, hepatovirus and parechoviruses contain 60 copies each of four polypeptide chains: VP1, VP2, VP3, and VP4. These chains are elements of protein subunits called mature "protomers". The protomer is defined as the smallest identical subunit of the virus. Traces of a fifth protein, VPO, which is cleaved to VP2 and VP4 are also observed. Together, these proteins form the shell or coat of poliovirus.

The picornaviral genome consists of a single strand of messenger-active RNA. The genomic messenger active RNA consists of a "+" strand which is polyadenylated at the 3' terminus and carries a small protein, VPg, covalently attached to the 5' end. The first picornaviral RNA to be completely sequenced and cloned into DNA was that of a type 1 poliovirus. However, polioviruses lack a 5'm$^7$GpppG cap structure, and the efficient translation of RNA requires ribosomal binding that is accomplished through an internal ribosomal entry site (IRES) within the 5' untranslated region (5'NTR).

The common organizational pattern of a poliovirus is represented schematically in FIG. 1, which comprises 5'NTR, P1, P2, P3 and 3'NTR with a polyadenylated tail. The 5'NTR comprises 6 domains arbitrarily designated as I, II, III, IV, V, and VI. The IRES comprises domains II–VI. P1 is the coding region for structural proteins also known as the capsid proteins. P2 and P3 encode the non-structural proteins. A schematic diagram of the six domains of the 5'NTR is represented in FIG. 2.

In nature, three immunologically distinct poliovirus types occur: serotype 1, 2, and 3. These types are distinct by specific sequences in their capsid proteins that interact with specific sets of neutralizing antibodies. All three types occur in different strains, and all naturally occurring types and strains can cause poliomyelitis. They are, thus, neurovirulent. The genetic organization and the mechanism of replication of the serotypes are identical; the nucleotide sequences of their genomes are >90% identical. Moreover, all polioviruses, even the attenuated vaccine strains, use the same cellular receptor (CD155) to enter and infect the host cells; and they express the same tropism for tissues in human and susceptible transgenic animals.

The neuropathogenicity of poliovirus can be attenuated by mutations in the regions specifying the P1 and P3 proteins as well as in the internal ribosomal entry site (IRES) within the 5'NTR. The Sabin vaccine strains of type 1, 2, and 3 carry a single mutation each in domain V of their IRES elements that has been implicated in the attenuation phenotype. Despite their effectiveness as vaccines, the Sabin strains retain a neuropathogenic potential in animal models for poliomyelitis. Albeit at a very low rate, they can cause the disease in vaccinees.

Indeed, the single point mutations in the IRES element of each Sabin vaccine strain can revert in a vaccinee within a period of 36 hours to several days. Overall, vaccine associated acute poliomyelitis occurs in the United States at a rate of 1 in 530,000 vaccinees. The polioviruses isolated from vaccinated patients with poliomyelitis may also have mutations reverted in different positions of their genomes. Wimmer, E., et al., *Ann.Rev.Gen.*, 27:353–436 (1993), Minor, P. D., supra.

Recombinant Polioviruses

Chimeric polioviruses carrying heterologus IRES elements, which have lost their inherent neuropathogenic potential have been described . Gromeier, M., et al., *Proc. Natl. Acad. Sci. USA*, 93:2370–2375 (1996), incorporated herein by reference. It was found that the substitution of the cognate IRES of poliovirus with its counterpart from Human Rhinovirus type 2 (HRV2) eliminated the ability of the resulting chimera, PV1(RIPO) to grow within cells of neuronal derivation (FIGS. 3A and B). The inventors also described the construction of and neurovirulence testing of a chimera carrying the P1 coding region for the structural proteins derived from PV1(S), PV1(RIPOS) in addition to the heterologous IRES originating from HRV2.

The non-pathogenic phenotype of PV1(RIPO) and PV1 (RIPOS) was documented in mice transgenic for the human poliovirus receptor, CD155 tg mice. See Gromeier et al., supra. It was shown that non-pathogenic PV/HRV2 IRES chimeras are unable to cause the typical lesions of the spinal cord typical of poliomyelitis when injected intracerebrally into CD155 tg mice. The non-pathogenic property of these constructs are now shown in Cynomolgus monkeys (FIG. 3A). The non-human primates that received intraspinal inoculations of PV1(RIPO) or PV1(RIPOS) remained unaffected or developed transient, subtle pareses of one foot in an isolated case. Permanent neurological dysfunction or signs of poliomyelitic disease were not noticed in any of the treated monkeys.

Despite its inability to replicate efficiently within cells of neuronal origin, it is now shown that PV1(RIPO) retained wild-type growth characteristics with an ability to lyse tumor cells in a panel of rapidly dividing malignant cell types originating from human malignancies (FIGS. 10–17).

OBJECTIVES OF THE INVENTION

It is an objective of the present invention to develop non-neuropathogenic polioviruses for the treatment for various types of cancer, in particular cancer of the central nervous system.

It is a further objective of the present invention to treat cancer cells by infecting them with a nonpathogenic poliovirus to cause cancer cell lysis and death.

It is another objective of the present invention to develop further novel poliovirus chimeras, which would be suitable for the treatment of cancer.

It is a further objective of the present invention to develop further novel poliovirus chimeras, which would be suitable for the treatment and cure of gliomas, in particular glioblastomas.

LIST OF REFERENCES

1. Leibel, S. A., et al., *Cancer*, 35:1551–1557 (1975).
2. Walker, M. D., et al., *J. Neurosurg*., 49:333–343 (1978).
3. Chang, C. H., et al., *Cancer*, 52:997–1007 (1983).
4. Bloom, H. J. G., *Int. J. Radiat. Oncol. Biol. Phys*., 8:1083–1087 (1982).
5. Choucair, A. K., et al., *J. Neurosurg*., 65:654–658 (1986).
6. Miller, A. D., *Nature*, 357:455–460 (1992).
7. Martuza, R. L., et al., *Science*, 252:854–856 (1991).
8. Bischoff, J. R., *Science*, 274:373–376 (1996).
9. Wood, M. J. A., et al., *Gene Therapy*, 1:283–29, (1994).
10. Markert, J. M., et al., *Neurosurgery*, 32:597–603 (1993).
11. Mineta T., et al., *Nature Medicine*, 1:938–943 (1995).
12. Andreansky, S., et al., *Cancer Res*., 57:1502–1509 (1997).
13. Izquierdo, M., et al., *Gene Therapy*, 2:66–69 (1995).
14. Chen, S. H., et al., *PNAS*, USA, 91:3054–3057 (1994).
15. Kandel, E. R. and Schwartz, J. H., ed. *Principles of Neural Science*, Chapter 2, pp. 14–23 Elsevier/North, Holland, 1981.
16. Black, I., ed. *Cellular and Molecular Biology of Neuronal Development*, Chapter 2, pp. 29–47, Plenum Press, New York, 1984.
17. Bodian, D., *Diseases of the Nervous System*, Chapter 170 pp.2323–2339, McGraw Hill, New York.
18. Ren, R., et al., *Cell*, 63:353–362 (1990).
19. Koike, S., et al., *PNAS*, USA, 88:951–955 (1991).
20. Sabin & Boulger, *Dev. Biol. Stand*., 1:115–118 (1973).
21. Minor, P. D., *Dev. Biol. Stand*., 78:17–26 (1993).
22. Wimmer, E., et al., *Ann. Rev. Gen*., 27:353–436 (1993).
23. Gromeier, M., et al., *Proc. Natl. Acad. Sci*. USA, 93:2370–2375 (1996).
24. Sambrook, Fritsch and Maniatis, *Molecular Cloning*, Cold Spring Harbor Laboratory Press, N.Y. (1989).
25. Wimmer, et al., U.S. Pat. No. 5,674,729.
26. Omata, T., et al., *J. Virol*., 58:348–358 (1986).
27. WHO Technical Report Series No. 80 (1990).
28. Kawamura, N., et al., *J Virol*., 63:1302–1309 (1989).
29. Fogh, J., et al., *J. Natl. Cancer Inst*., 59:221–226 (1997).
30. Agol , et al., *J. Virol*., 63:4034–4038 (1989).
31. LaMonica, N. and Rancaniello, V. R., *J. Virol*., 63:2357–2360 (1989).
32. Reed and Muench, *Am. J. Hyg*., 27:493–495 (1938).

SUMMARY OF THE INVENTION

According to the present invention, non-neuropathogenic, oncolytic, chimeric recombinant polioviruses have been engineered. The oncolytic chimeric polioviruses comprise:

A recombinant poliovirus constructed from a poliovirus having a 5'NTR region containing an internal ribosomal entry site (IRES), and the coding sequences for structural proteins (P1), and for the non-structural proteins (P2 and P3) and a 3'NTR selected from the group consisting of wild type serotype 1, serotype 2, and serotype 3, wherein a. i. a part of the IRES of the poliovirus is substituted with a part of the IRES of Human Rhinovirus serotype 2 also having a 5'NTR region containing an internal ribosomal entry site (IRES), the coding sequences of structural proteins (P1), and for the non-structural proteins (P2 and P3) and a 3'NTR, or ii. at least a part of the IRES of the poliovirus is substituted with at least a part of the IRES of a virus selected from the group of picornaviruses comprising Human Rhinovirus serotype 1, 3–100, coxsackievirus serotype B1–B6, human echovirus serotype 1–7, 9, 11–27, 29–33, all of which also having a 5'NTR region containing an internal ribosomal entry site (IRES), the coding sequences of structural proteins (P1), and for the non-structural proteins (P2 and P3) and a 3'NTR, and wherein b. optionally, at least a part of the P1 of the poliovirus is substituted respectively with at least a part of the P1 of a Poliovirus (Sabin), selected from the group consisting of PV1(S), PV2(S) and PV3(S);

c. optionally, at least a part of the P3 of the poliovirus is substituted with at least a part of the P3 of Poliovirus (Sabin), selected from the group consisting of PV1(S), PV2(S) and PV3(S); and d. optionally, at least a part of the 3'NTR of the wild type poliovirus is substituted with at least a part of the entire 3'NTR of poliovirus (Sabin), selected from the group consisting of PV1(S), PV2(S), and PV3(S).

The invention is further directed to a therapeutic method of treating malignant tumors comprising the steps:

A. Preparing a nonpathogenic recombinant poliovirus having a 5'NTR region containing an internal ribosomal entry site (IRES), and the coding sequences for structural proteins (P1), and for the non-structural proteins (P2 and P3) and a 3'NTR selected from the group consisting of wild type serotype 1, serotype 2, and serotype 3, by a. substituting at least a part of the IRES of the poliovirus with at least a part of the IRES of a virus selected from the group of picornaviruses comprising Human Rhinovirus serotype 1–100, coxsackievirus serotype B1–B6, human echovirus serotype 1–7, 9, 11–27, 29–33, all of which also having a 5'NTR region containing an internal ribosomal entry site (IRES), the coding sequences of structural proteins (P1), and for the non-structural proteins (P2 and P3) and a 3'NTR;

b. optionally substituting at least a part of the P1 of the poliovirus with at least a part of the P1 of a Poliovirus (Sabin), selected from the groups consisting of PV1(S),PV2(S) and PV3(S);

c. optionally substituting at least a part of the P3 of the poliovirus with at least a part of the P3 of Poliovirus (Sabin), selected from the groups consisting of PV1(S), PV2(S) and PV3(S);

d. optionally, substituting at least a part of the 3'NTR of the poliovirus with at least a part of the 3'NTR of poliovirus (Sabin), selected from the group consisting of PV1(s), PV2(S), and PV3(S); and B. Administering intravenously, intrathecally or directly to the tumor site a composition comprising the recombinant poliovirus.

BRIEF DESCRIPTION OF THE DRAWINGS

FIGS. 3A and 3B demonstrate the results of neuropathogenicity testing of PV1(RIPO) and PV1(RIPOS) in CD155 tg mice as well as in Cynomolgous monkeys. FIG. 3A shows the results of intraspinal inoculation. FIG. 3B shows the result of the intravenous and intracerebral inoculations.

FIG. 5 is a schematic representation of PV/HRV2 IRES chimeras (HRV2- specific sequences are boxed). All chimeras feature the cloverleaf (5'NTR domain I), open reading frame and 3'NTR of PV1(M). The right hand column provides neuropathogenic indices obtained by intracerebral inoculation of individual recombinants into CD155 tg mice.

FIGS. 6A and 6B show one-step growth curves of those PV/HRV2 IRES chimeras that were found to be of attenuated neurovirulence in CD155 tg mice in SK-N-MC cells (FIG. 6A) and HeLa cells (FIG. 6B). For genetic structure see FIG. 5. For comparison, growth kinetics of the neuropathogenic PV1(M) are included. Note that the non-neuropathogenic phenotype in experimental animals of PV1 (R2–4, 6), PV1(R5), PV1(R5–6), PV1(R2–5), and PV1(R6) in CD155 tg mice (FIG. 5) is also evident in tissue culture.

FIG. 7 depicts the IRES sequence and bigeneric structure of PV1(prr) carrying the IRES of PV1(M) where the terminal loop regions of domain V (nt #484–nt #508) and domain VI (nt #594–nt #612) have been substituted with the corresponding fragments of HRV2 (boxed sequences are derived from HRV2, the remaining sequences are from PV1(M)). A restriction site for endonuclease KpnI that was introduced for cloning purposes is boxed. The initiating AUG triplet is shown in white letters.

FIGS. 8A and 8B show growth kinetics of PV1(prr) in SK-N-MC neuroblastoma (FIG. 8A) and HeLa (FIG. 8B) cells in comparison to those of PV1(M) and PV1(RIPO). FIG. 8C demonstrates the results of an analysis of neuropathogenicity of PV1(prr) in CD155 tg mice.

FIGS. 18A–18E are photomicrographs of histological sections through subcutaneously implanted glioblastomas (cell line HTB-15) in athymic mice. FIGS. 18A, 18C, and 18E show a tumor from an untreated mice that had been growing for about 60 days. FIGS. 18B, 18D, and 18F are brain sections from a fellow mouse treated with a single intraneoplastic inoculation of PV1(RIPO) 30 days after tumor implantation show the dramatic results of therapy with oncolytic oliovirus recombinants.

FIG. 20A shows the results with no treatment. FIG. 20B shows the results for mice which were treated intramuscularly with $5 \times 10^7$ pfu PV1(RIPO) (FIG. 20B). FIG. 20C shows the results of mice that were treated intravenously with $5 \times 10^7$ pfu of PV1(RIPO). FIG. 20D shows the results of intracerebral administration of the same amount of recombinant virus, demonstrating a cure.

FIGS. 22A–22C are detailed views of sections depicted in FIG. 21. FIG. 22A is a section through the lateral ventricle of a normal mouse shows the detached intact ependymal lining of the intact ventricle wall. FIG. 22B is a section of untreated athymic mice with glioma implant harbors globular neoplastic masses that are attached alongside the ventricle walls. FIG. 22C shows that lesions like the one shown in FIG. 22B are destroyed upon treatment of tumor-bearing athymic mice with PV1(RIPO). Only the remains of a vigorous host reaction against the invading tumor leaving a paraventricular parenchymal lesion indicating the site where a tumor fragment had attached to the ventricular wall.

DETAILED DESCRIPTION OF THE INVENTION

Figure 1:
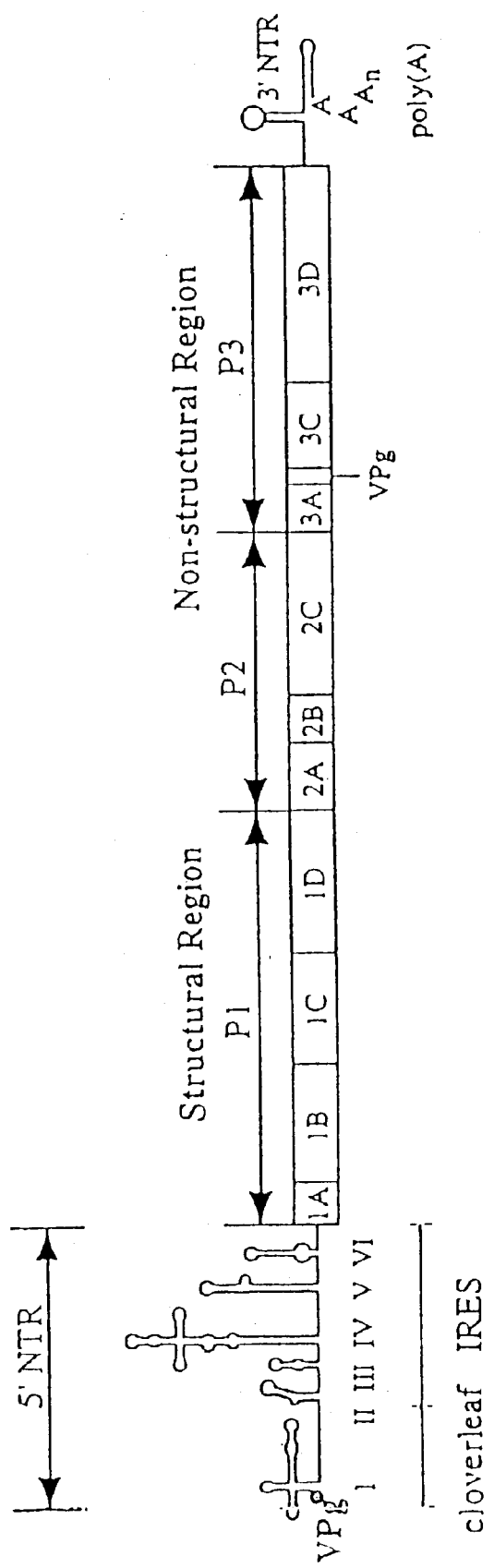
FIG. 1 depicts the genomic organization of poliovirus. The viral RNA is covalently linked to a genome-linked protein, VPg.5'NTR domain I is also known as the cloverleaf. The open reading frame is divided into coding regions for the structural (capsid) proteins (P1) and the non-structural proteins (P2 and P3). Individual 5'NTR domains are indicated by roman numerals.
Figure 2:
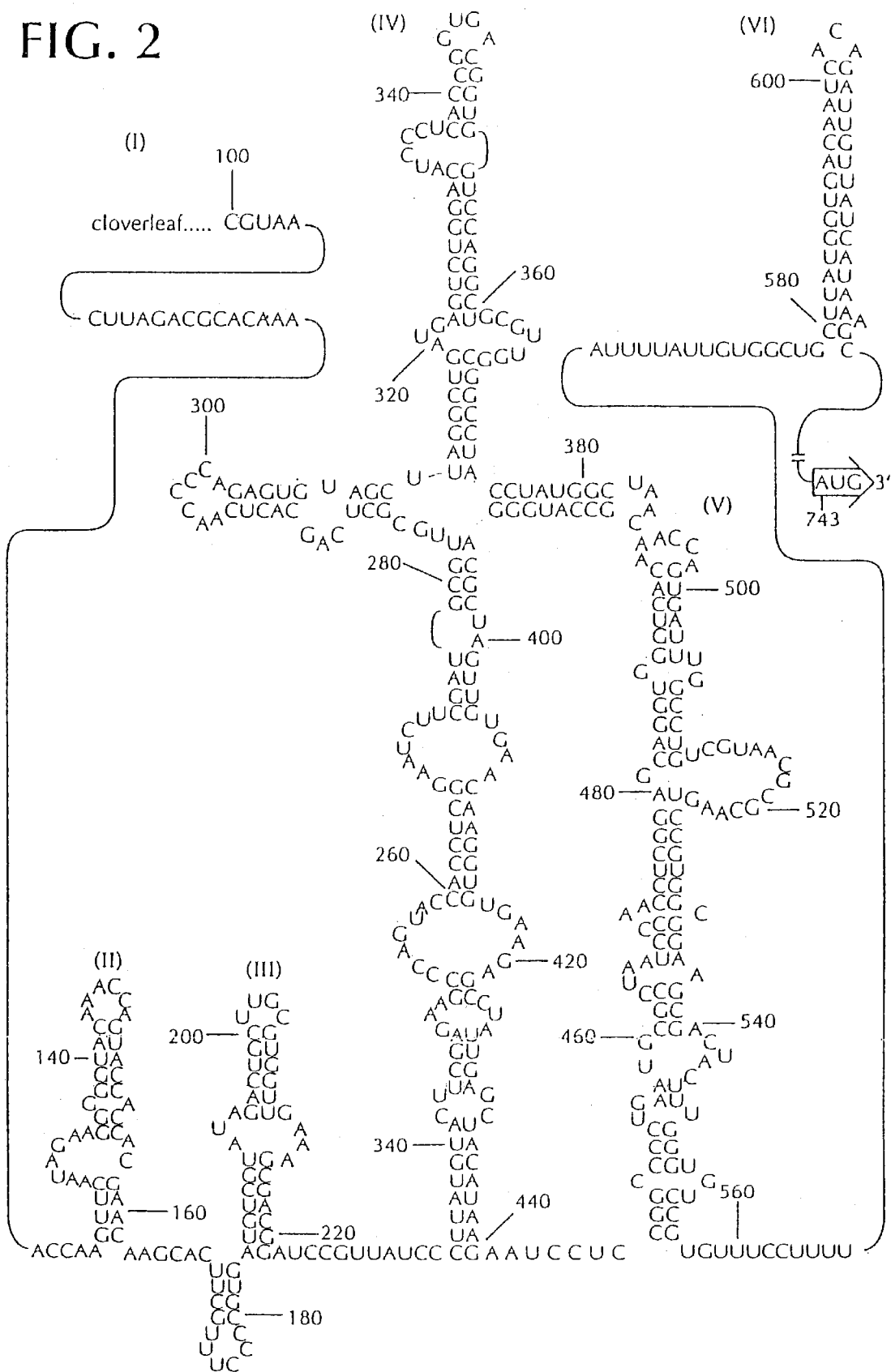
FIG. 2 is a representation of the predicted secondary structure of the poliovirus IRES (sequence and nucleotide numbering of PV1(M)). All picornaviruses (including poliovirus-and HRV) feature IRES elements within their respective 5'NTRs. Poliovirus IRESes like their counterparts from the genus rhinovirus are type 1 IRESes. Wimmer, et al., supra. Domains are numbered with roman numerals. The 154 nt spacer separating a conserved silent AUG triplet within the base stem loop VI (nt #583) from the initiating AUG (position #743) has been omitted.

According to the present invention non-neuropathogenic oncolytic poliovirus chimeras have been bio-engineered for the treatment of malignant tumors in various organs. The non-neuropathogenic oncolytic poliovirus chimeras comprise A recombinant poliovirus constructed from a poliovirus having a 5'NTR region containing an internal ribosomal entry site (IRES), and the coding sequences for structural proteins (P1), and for the non-structural proteins (P2 and P3) and a 3'NTR selected from the group consisting of wild type serotype 1, serotype 2, and serotype 3, wherein a. i. a part of the IRES of the poliovirus is substituted with a part of the IRES of Human Rhinovirus serotype 2 also having a 5'NTR region containing an internal ribosomal entry site (IRES), the coding sequences of structural proteins (P1), and for the non-structural proteins (P2 and P3) and a 3'NTR, or ii. at least a part of the IRES of the poliovirus is substituted with at least a part of the IRES of a virus selected from the group of picornaviruses comprising Human Rhinovirus serotype 1–100, coxsackievirus serotype B1–B6, human echovirus serotype 1–7, 9, 11–27, 29–33, all of which also having a 5'NTR region containing an internal ribosomal entry site (IRES), the coding sequences of structural proteins (P1), and for the non-structural proteins (P2 and P3) and a 3'NTR, and wherein b. optionally, at least a part of the P1 of the poliovirus is substituted with at least a part of the P1 of a Poliovirus (Sabin), selected from the group consisting of PV1(S), PV2(S) and PV3(S);

c. optionally, at least a part of the P3 of the poliovirus is substituted with at least a part of the P3 of Poliovirus (Sabin), selected from the group consisting of PV1(S), PV2(S) and PV3(S); and d. optionally, at least a part of the 3'NTR of the poliovirus is substituted with at least a part of the 3'NTR of poliovirus (Sabin), selected from the group consisting of PV1(S), PV2(S), and PV3(S).

The invention is further directed to a therapeutic method of treating malignant tumors comprising the steps:

A. Preparing a recombinant poliovirus constructed from a poliovirus having a 5'NTR region containing an internal ribosomal entry site (IRES), and the coding sequences for structural proteins (P1), and for the non-structural proteins (P2 and P3) and a 3'NTR selected from the group consisting of wild type serotype 1, serotype 2, and serotype 3, by a. substituting at least a part of the IRES of the poliovirus with at least a part of the IRES of a virus selected from the group of picornaviruses comprising Human Rhinovirus serotype 1–100, coxsackievirus serotype B1–B6, human echovirus serotype 1–7, 9, 11–27, 29–33, all of which also having a 5'NTR region containing an internal ribosomal entry site (IRES), the coding sequences of structural proteins (P1), and for the non-structural proteins (P2 and P3) and a 3'NTR;

b. optionally substituting at least a part of P1 of the poliovirus with at least a part of the P1 of a Poliovirus (Sabin), selected from the group consisting of PV1(S), PV2(S) and PV3(S);

c. optionally substituting at least a part of the P3 of the poliovirus with at least a part of the P3 of Poliovirus (Sabin), selected from the group consisting of PV1(S), PV2(S) and PV3(S);

d. optionally, substituting at least a part the 3'NTR of the poliovirus with at least a part of the 3'NTR of poliovirus (Sabin), selected from the group consisting of PV1(s), PV2(S), and PV3(S);and B. Administering directly to the tumor site or intravenously a composition comprising the recombinant poliovirus.

Structure and Characteristics of Recombinant Polioviruses

Figure 4:
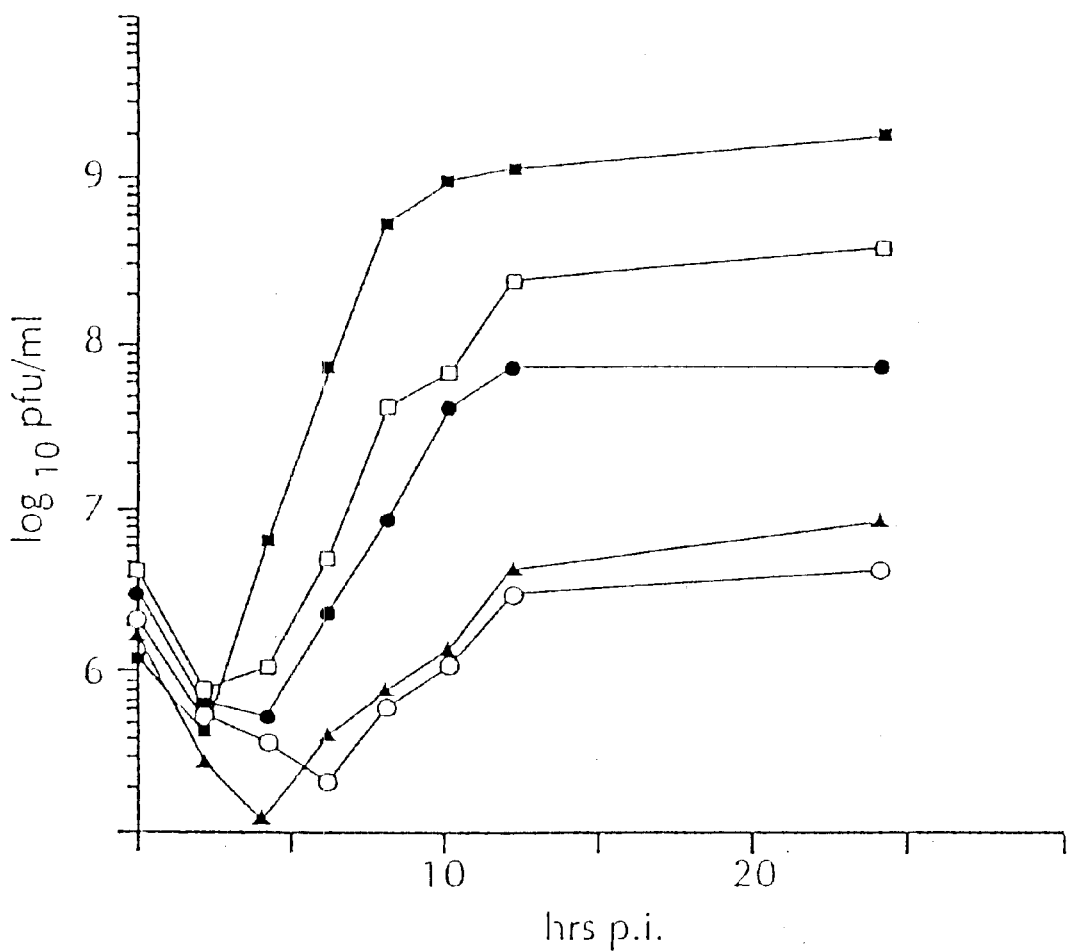
FIG. 4 presents one-step growth curves in SK-N-MC neuroblastoma cells of IRES chimeras featuring the IRES elements of Human Rhinovirus type 2 and type 14 (HRV2 and 14). Coxsackievirus B4 (CB4) and Echovirus 9 (E9) with poliovirus P1, P2 and P3 respectively. Growth properties in HeLa cells of all these recombinants were undistinguishable from those of wild-type poliovirus (data not shown).
Figure 9:
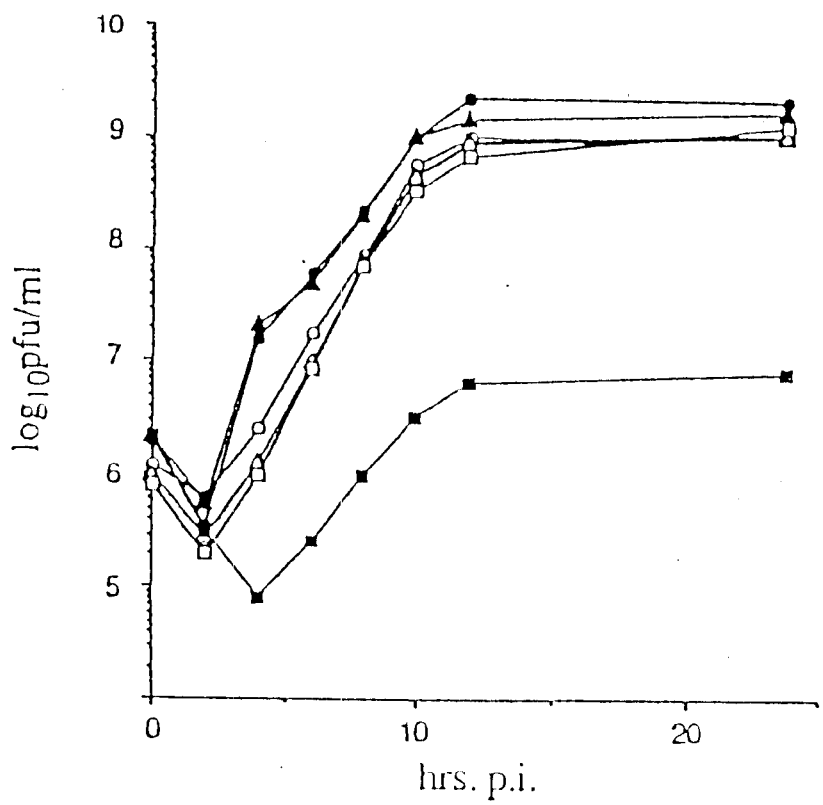
FIG. 9 are one-step growth curves of PV1(M) (open symbols) and PV1(RIPO) (solid symbols) in HTB-14 (circles) and HTB-15 (triangles) glioblastoma cell lines, and in SK-N-MC neuroblastoma (squares) cells. The efficient replication of PV1(RIPO) in glioblastoma cells is in sharp contrast with the poor growth capacity in neuroblastoma cells.
Figure 11:
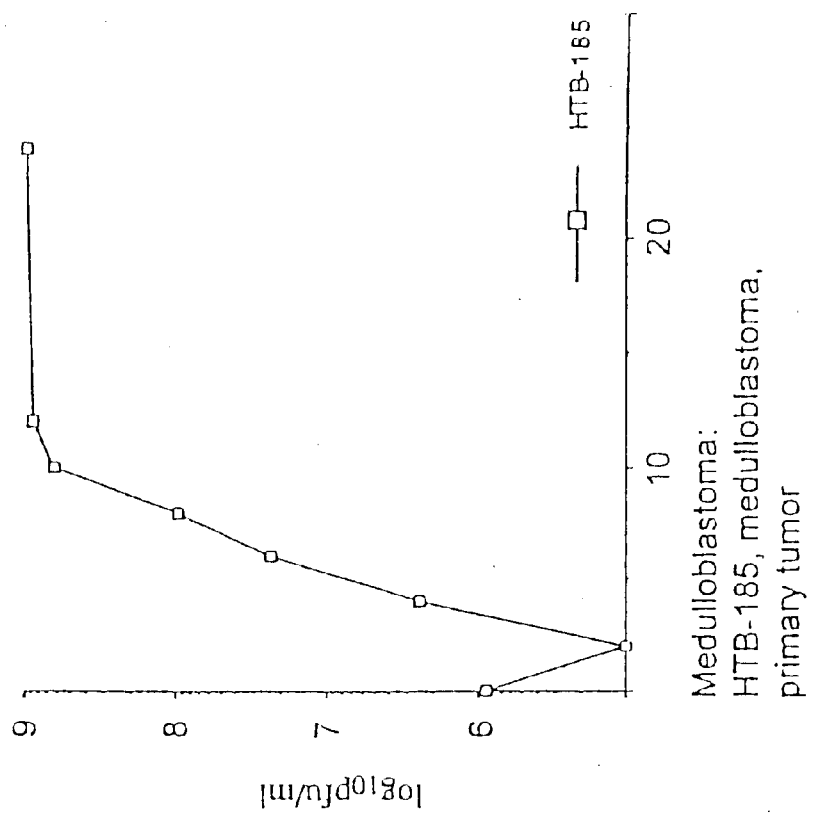
FIG. 11 one-step growth curves of PV1(RIPO) in a medulluoblastoma cell line.
Figure 10:
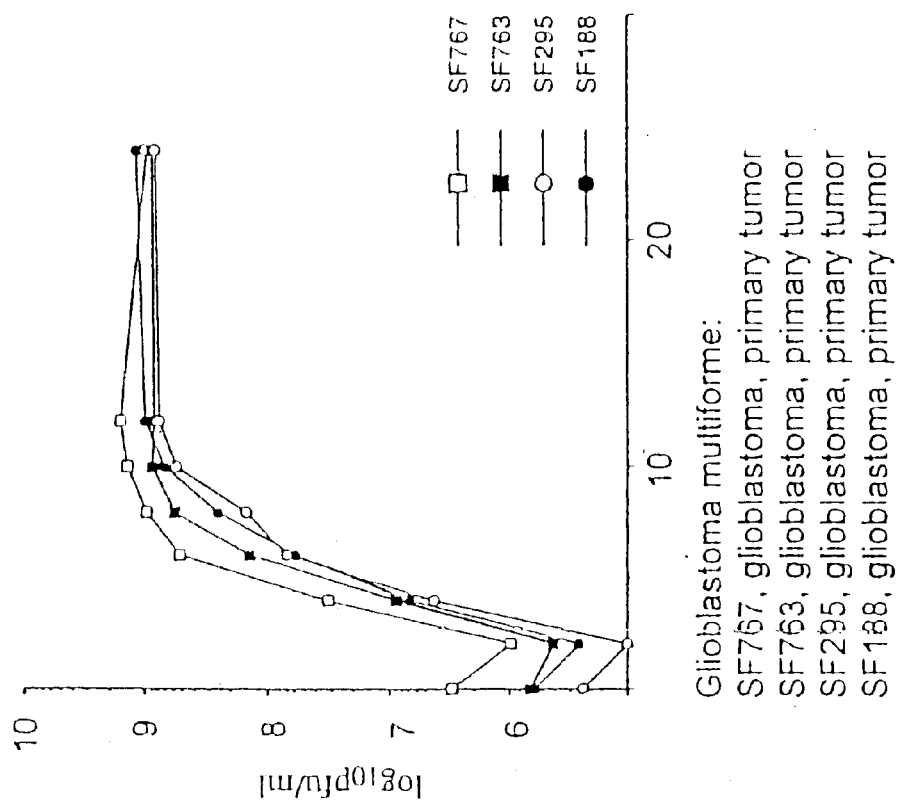
FIG. 10 one-step growth curves of PV1(RIPO) in a panel of different glioblastoma cell lines.
Figure 13:
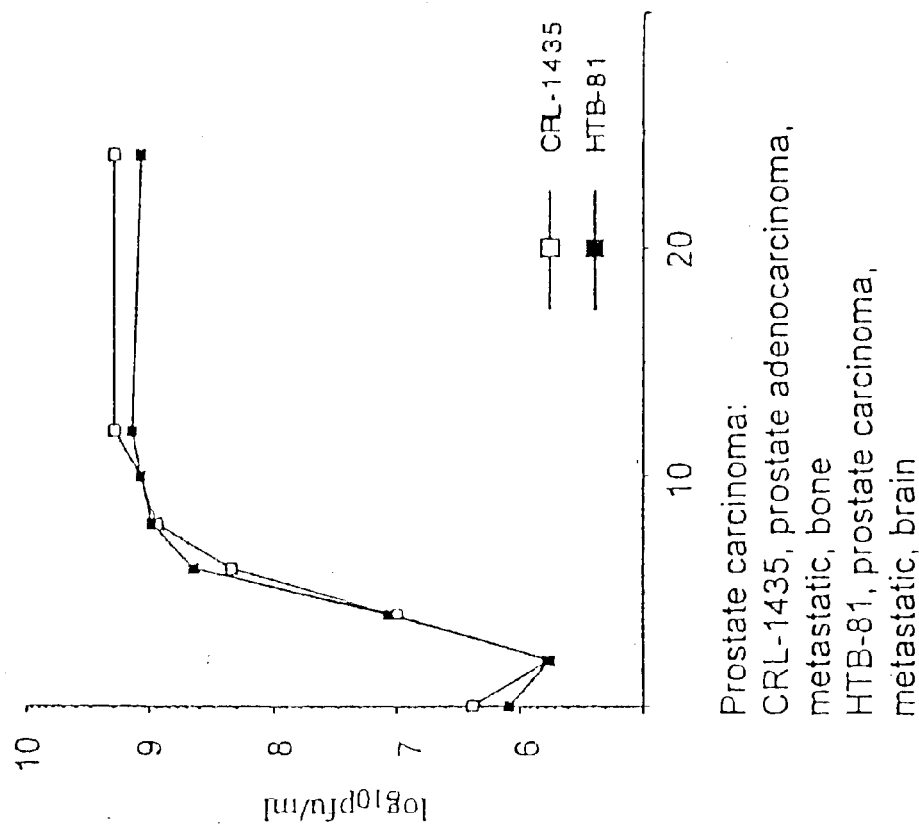
FIG. 13 one-step growth curves of PV1(RIPO) in prostate carcinoma cell lines.
Figure 12:
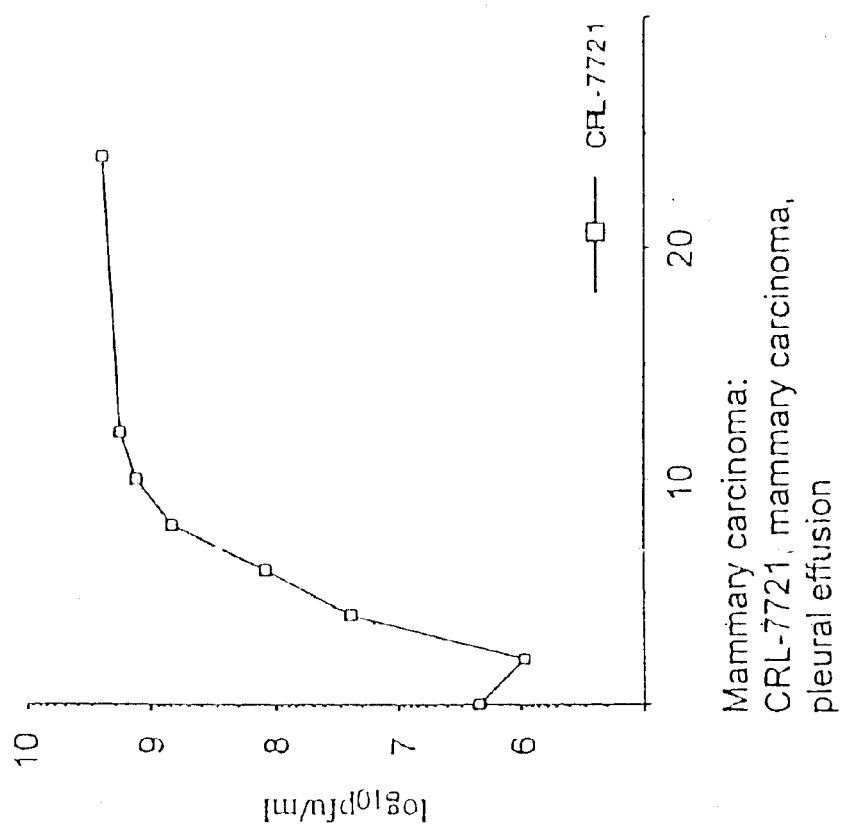
FIG. 12 one-step growth curves of PV1(RIPO) in a mammary carcinoma cell line.
Figure 15:
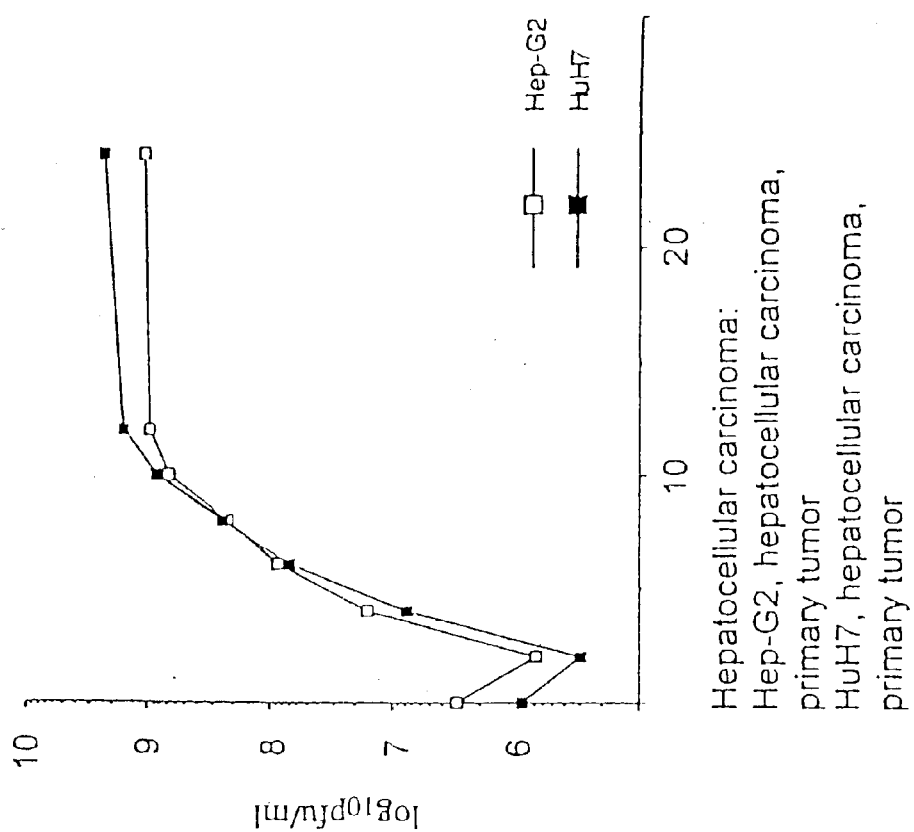
FIG. 15 one-step growth curves of PV1(RIPO) in hepatocellular carcinoma cell lines.
Figure 14:
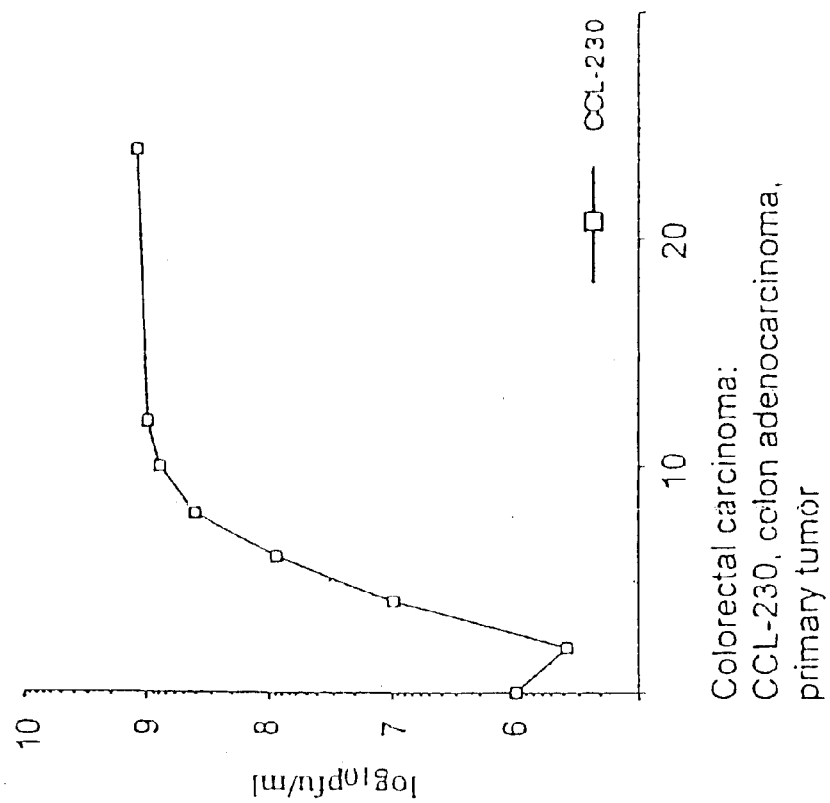
FIG. 14 one-step growth curves of PV1(RIPO) in a colorectal carcinoma cell line.
Figure 17:
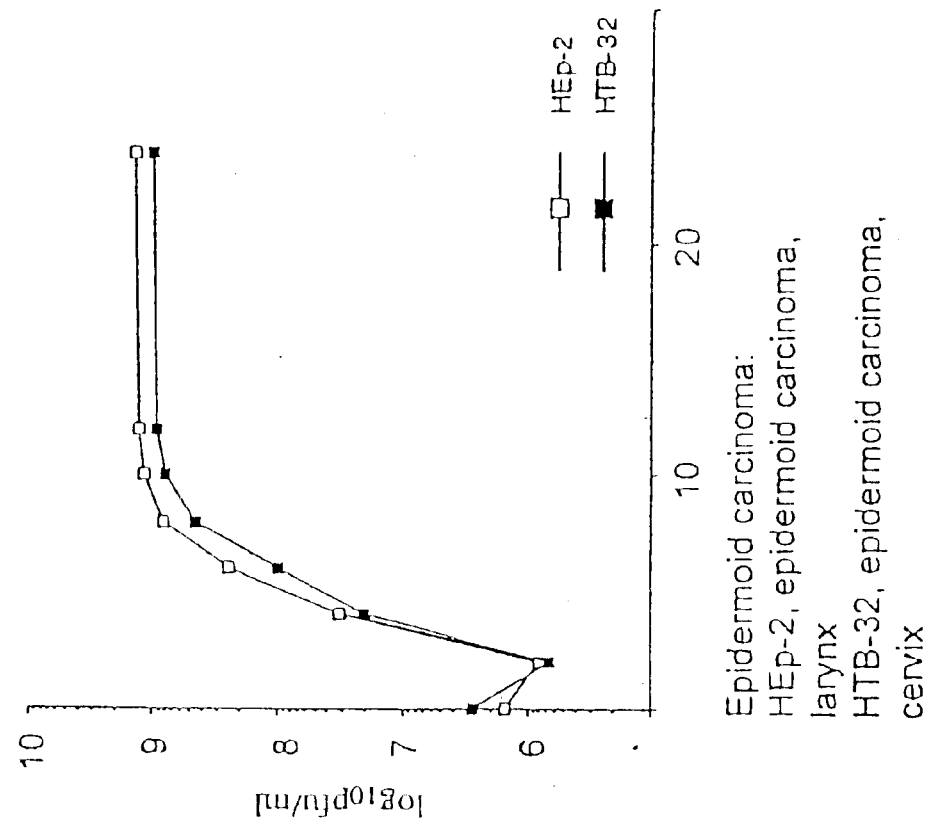
FIG. 17 one-step growth curves of PV1(RIPO) in epidermoid carcinoma cell lines.
Figure 16:
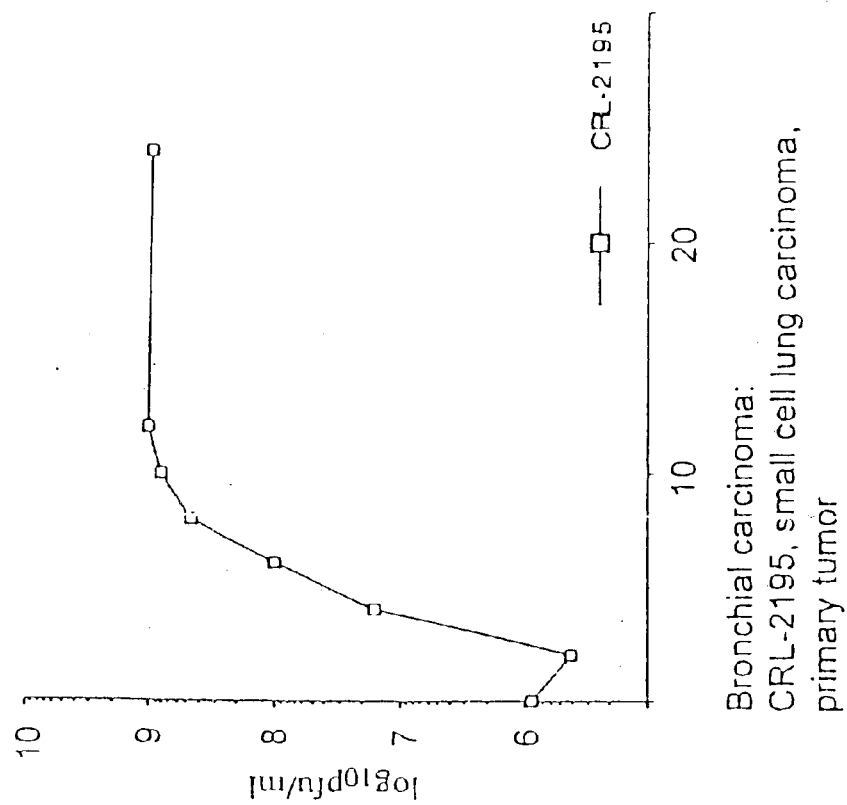
FIG. 16 one-step growth curves of PV1(RIPO) in a bronchial carcinoma cell line.
Figure 18D:
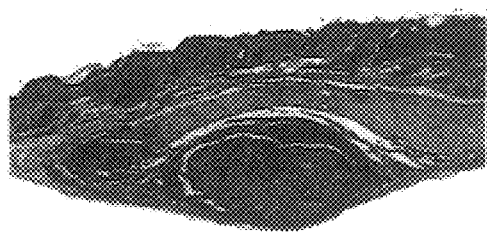
Figure 18E:
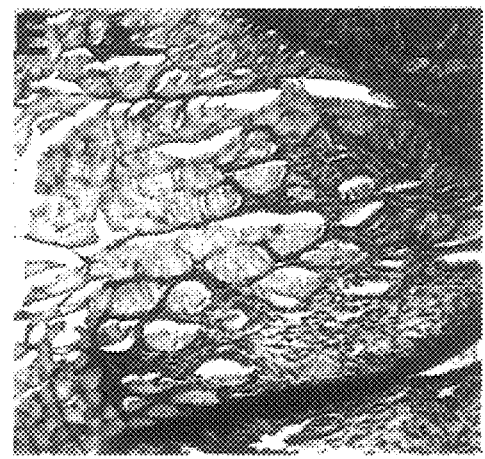
Figure 18F:
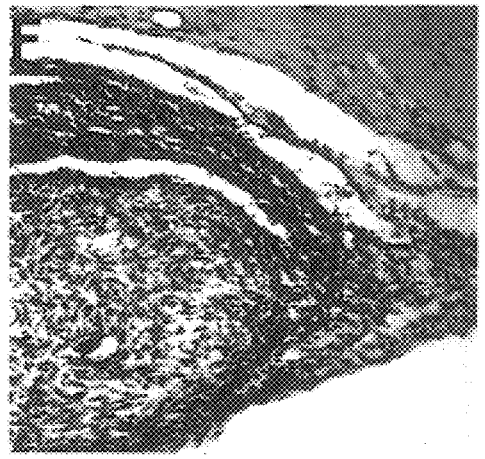

A prototype non-pathogenic poliovirus chimera has been generated by exchanging the native IRES of type 1 poliovirus (Mahoney) with its counterpart from Human Rhinovirus type 2 (HRV2), yielding PV1(RIPO). Other IRES chimeras have been developed using the procedure which led to the construction of PV1(RIPO). The exchange of the poliovirus IRES with any of the IRES elements derived from the group of viruses comprising Human Rhinovirus type 1, 3–100, Coxsackievirus B1–B6(CB), and Echovirus type 1–7, 9, 11–27 and 29–33 is expected to provide a recombinant poliovirus chimeras with a reduced ability to replicate within cells of neuronal origin to lyse them. This is demonstrated by the one-step growth curves of IRES chimeras of PV1(M) with HRV14 (PV/HRV14), with CB4 (PV/CB4), and with E9 (PV/E9) in SK-N-MC cells (FIG. 4). The reduction or elimination of non-neurocytopathogenic phenotype of poliovirus IRES chimeras was confirmed in studies using CD155 tg mice (data not shown)

Novel non-neuropathogenic, oncolytic, recombinant chimeras of PV, PV(S) and HRV2 have been further constructed. In the novel chimeric polioviruses only a portion of the IRES of a wild type poliovirus, such as PV1(M), has been substituted with the corresponding portion of HRV2 (FIG. 5). In order to identify the specific portions, which are replaced, the known domains II, III, IV, V, and VI of the IRES have been utilized. In PV1(R2–4,6) domains II, III, IV, and VI of PV1(M) were replaced with the domains II, III, IV and VI have been utilized. In PV1(R2–4, 6) domains II, III, IV, and VI of PV1(M) were replaced with the domains II, III, IV and VI of HRV2; in PV1(R5); the domain V of PV1(M) was replaced with the domain V of HRV2; etc. Polioviruses that carry bi-generic IRESes composed of sequence elements derived from the IRES domains V and VI of HRV2 and PV1, respectively (see FIG. 5), are characterized by a loss of neuropathogenic potential when tested in CD155 tg mice (FIG. 5). This phenotype was also evident when one-step growth curves of these chimeras were establish in SK-N-MC neuroblastoma cells (FIG. 6A)

Figure 7:
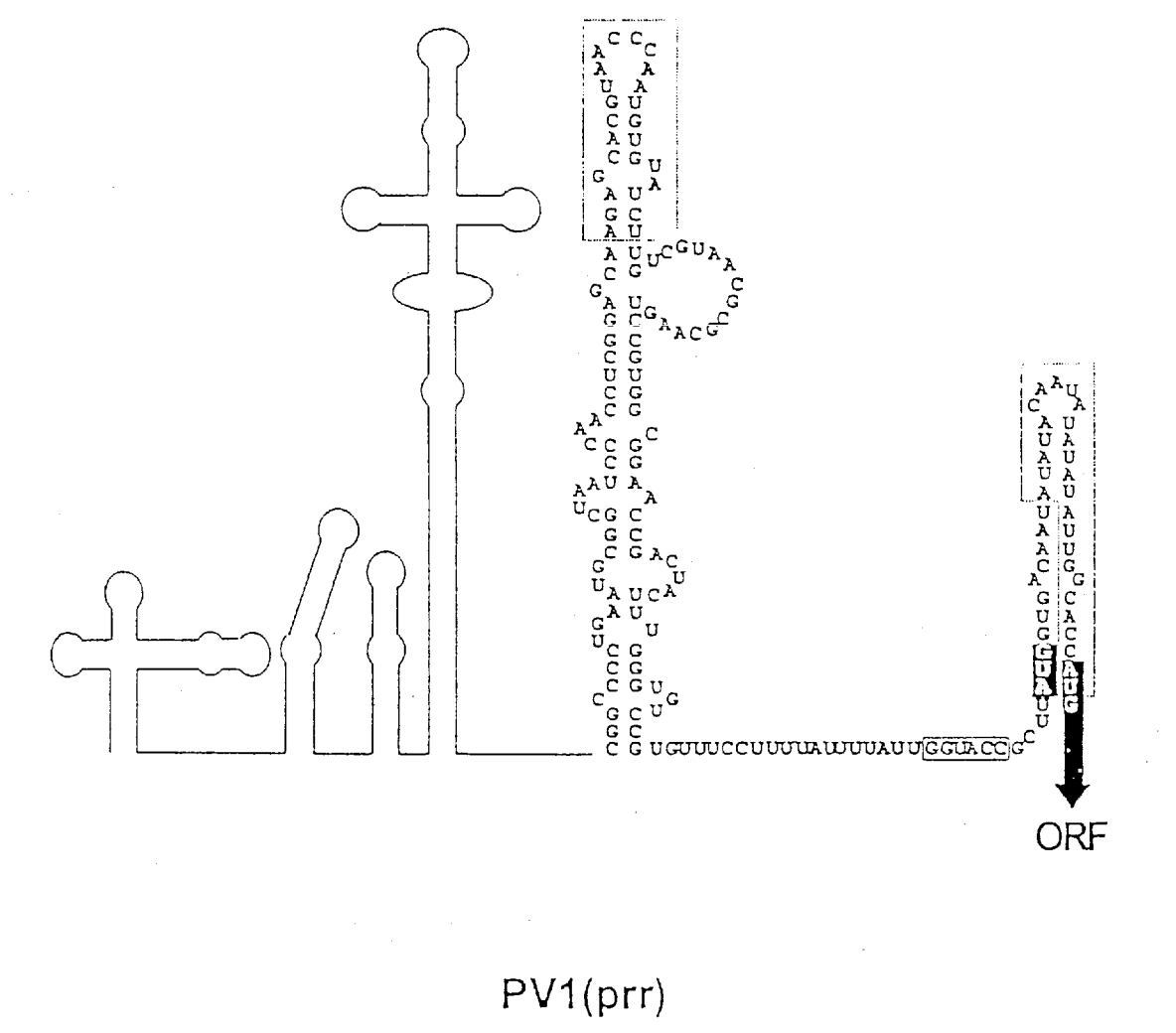

The poliovirus recombinants which are suitable for the present invention feature a loss of neuropathogenic potential and hence are safe to use in human therapy. Ablated neuropathogenicity was documented in CD155 tg mice and non-human primates (FIG. 3) and in SK-N-MC neuroblastoma cells in vItro (FIG. 6). The non-neuropathogenic oncolytic poliovirus recombinants are those wherein the IRES of wild type poliovirus has been replaced with the IRES of HRV2. The replacement may be in whole as in PV1(RIPO), or the replacement may be in part, wherein a portion of the IRES of the wild type poliovirus is replaced with the corresponding portion of the IRES of HRV2. For example, suitable chimeras may be represented as PV1 (R2–4, 6), PV1(R5), PV1(R2–5), PV1(R5–6), PV1(R6) and PV1(prr). PV1(prr) is a poliovirus recombinant wherein nucleotides 484–508 (nt #484–nt #568) of domain V and nucleotides 594–612 (nt #594–nt #612) of domain VI of the IRES of wild type poliovirus were replaced with their counterpart nt #484–nt #508 of domain V and nt #594–nt #612 of domain VI from HRV2. See FIG. 7. PV1(ppr) was characterized by a loss of neuropathogenicity, demonstrated by its reduced ability to propagate within cells of neuronal origin and failure to cause neurological disease in CD155 tg mice (FIG. 8). The preferred poliovirus chimeras for the purposes of the invention are PV1(RIPO) and PV1(RIPOS).

In addition to the IRES element, a part of or the entire coding region for the structural proteins (P1), non-structural proteins (P3) and/or the 3'NTR of the wild type PV may be replaced with the corresponding part of or the entire coding region for the structural proteins (P1), non-structural proteins (P3) and/or the 3'NTR of any virus strain of the group comprising PV1(S), PV2(S) and PV3(S). It is known that important genetic determinants for attenuation of neurovirulence may reside within the coding regions for the capsid proteins (P1), the non-structural protein (P3) or the 3'NTR of the Sabin strains of poliovirus. Inclusion of these genetic markers residing within the coding regions for P1, P3 or the 3'NTR into oncolytic non-pathogenic polioviruses will further ensure the ablation of neurovirulence of the poliovirus recombinants or chimeras of the present invention.

Synthesis of Recombinant Polioviruses

Recombinant poliovirus chimeras can be synthesized by well-known recombinant DNA techniques. Any standard manual on DNA technology provides detailed protocols to produce the poliovirus chimeras of the invention. Sambrook, Fritsch and Maniatis, *Molecular Cloning*, Cold Spring Harbor Laboratory Press, NY (1989).

The construction of a prototype recombinant poliovirus PV1(RIPO) was described in Gromeier, M., et al., supra. The cloning procedures used to produce oncolytic polioviruses with attenuated neurovirulence is generally as follows. Exemplary detailed cloning instructions for the construction of such recombinant viruses are provided in the Examples.

A cloning cassette, allowing for the convenient exchange of heterologous recombinant IRES elements into the poliovirus genome, is obtained through the introduction of engineered endonuclease restriction sites positioned at nt #110 (adjacent to the 5' border of the IRES element) and nt #747 latter restriction site, positioned within the open reading frame, is created through the introduction of silent mutations (described in Gromeier, M. et al., supra). The resulting cloning cassette can be used to easily integrate IREs elements:

(1) derived in toto from other virus species;

(2) generated by combining RNA structural domains from IRES elements of different virus species;

(3) generated by combining sequence fragments or individual nucleotides from different virus species;

(4) derived from eukaryotic sequences with IRES function; and (5) those that are entirely synthetic.

Experimental results show that composite IRES elements, constructed from individual structural domains or subdomain fragments originating from different virus species can replace the poliovirus IRES and give rise to novel recombinant viruses with favorable properties for the use as oncolytic agents.

These composite IRES elements are constructed through the use of polymerase chain reaction (PCR)-generated fragments. The fragments are those with cohesive ends forming endonuclease restriction sites that are either engineered or already present in the IRES sequence used. Sequences within IRES elements that allow for the introduction of novel endonuclease restriction sites through mutagenesis have been empirically identified. A detailed description for the cloning of exemplary composite IRES elements combining RNA structural domains or subdomain sequence elements derived from divergent virus species is given in the Examples 1 and 6.

A cloning cassette, allowing for the convenient exchange of the P1 coding region for the structural proteins with its counterparts from the group comprising PV serotype 1 (Sabin) is obtained through the introduction of an engineered endonuclease restriction site (by introduction of silent mutations) positioned at nt #3278, within the 5' most part of P2 bordering the 3' limit of P1. An engineered endonuclease restriction site positioned at nt #747 that has already been introduced with the purpose of convenient IRES exchange forms the 5' border of P1. Thus, the resulting cloning cassette, in addition to provide easy replacement of the IRES, can serve to integrate any desired P1 coding region selected from the group of polioviruses including the wild serotypes 1, 2 and 3, as well as the Sabin serotypes 1, 2 and 3. For this purpose, the P1 coding region from the selected strain is PCR amplified, making use of the cohesive ends generated by engineered endonuclease restriction sites defining the borders of P1 in the novel cloning cassette.

A cloning cassette, allowing for the convenient exchange of the coding region for the RNA-dependent RNA polymerase $3D^{pol}$ of poliovirus with its counterpart from a virus selected from the group comprising PV serotype 1 (Sabin), serotype 2 (Sabin), and serotype 3 (Sabin) in constructed as follows. Unique endonuclease restriction sites are introduced in the 5' most part of $3D^{pol}$ at nt #6060, upstream of any mutations within this coding region specific for any of the PV (Sabin) strains and in the 3' most part of $3D^{pol}$ at nt #7330, downstream of any mutations within this coding region specific for any in question can be integrated into the desired sequence encoding $3DP^{pol}$ produced by PCR amplification from the viral cDNA in question can be integrated into the cloning cassette making use of the introduced artificial restriction endonuclease recognition bordering the coding region for $3D^{pol}$.

A cloning cassette, allowing for the convenient exchange of the 3'NTR of poliovirus with the 3'NTR of the group comprising PV1(Sabin), PV2(Sabin), and PV3(Sabin) is constructed as follows. An engineered unique restriction site within the 3' most region of $3D^{pol}$, at nt #7330, has already been introduced for the creation of a cloning cassette for the convenient exchange of the coding region for $3DP^{pol}$. An additional restriction site is introduced at the very 3' border of the viral genome, immediately preceding the poly(A) tail from the 3' restriction site of the cloning cassette for easy exchange of the 3'NTR (nt #7439). PCR amplification of the desired 3'NTR from any given viral strain can easily be inserted into the cloning cassette making use of the engineered restriction sites defining in the 3' most part of P3 and immediately preceding poly(A).

Combining the genome modifications described above is obtained, a poliovirus cDNA with 4 independent cloning cassettes allowing for simple exchange of:

(1) IRES elements
(2) the coding region for the structural proteins P1
(3) the coding region for $3D^{pol}$
(4) the 3'NTR This "multipurpose cloning cassette" may be used to obtain recombinant polioviruses of the invention, including any poliovirus selected from the group of viruses comprising serotype 1, serotype 2 and serotype 3, wherein, a. at least a part of the IRES is substituted with at least a part of the IRES of a virus selected from the group of picornaviruses comprising Human Rhinovirus serotype 1–100, coxsackievirus serotype B1–B6, human echovirus serotype 1–7, 9, 11–27, 29–33, also having a 5'NTR region containing an internal ribosomal entry site (IRES), b. optionally, at least a part of P1 is substituted with the corresponding region of one of the viruses selected from the group consisting of PV1(S), PV2(S), and PV3(S);

c. optionally, at least a part of P1 is substituted with the corresponding region of one of the viruses selected from the group consisting of PV1(S), PV2(S), and PV3(S); and d. optionally, at least a part of the 3'NTR is substituted with the corresponding region of one of the viruses selected from the group consisting of PV1(S), PV2(S), and PV3(S).

Experiments are presented herebelow describing virus recombinants carrying composite IRES elements composed out of domains II, III, IV, V, VI derived from divergent virus species. The general cloning procedures for exemplifying intergeneric IRES domain recombinants (displayed in FIG. 5) are as follows (for detailed instructions, refer to Example 1).

Synthetic IRES elements that contain RNA structural domains derived from divergent virus species can be constructed if structural integrity essential for efficient IRES function is maintained. A series of intergeneric IRES domain and sub-domain recombinants that combine IRES sequence elements of polio and HRV2 have been developed. These recombinants IRESes can be produced through PCR amplification of desired IRES fragments using introduced endonuclease restriction sites for the formation of cohesive ends needed for cloning purposes as follows. PCR amplification using primers that carry recognition sites for endonucleases can produce individual IRES stem loops, or subdomain IRES fragments carrying cohesive ends for ligation into intact IRES units and subsequent integration into virus cDNA cloning cassettes. The position of mutations introduced for the creation of restriction endonuclease recognition sites has to be determined empirically, because they may interfere with IRES function. Suitable restriction sites that do not interfere with IRES function for the intergeneric IRES domain recombinants are provided in Example 6.

Similarly, additional modifications of IRES elements through the introduction of artificial endonuclease restriction sites may be introduced for the synthesis of novel intergeneric IRES chimeras that recombine sequence elements of different viruses in alternative ways. In addition to intergeneric domain recombinants, artificial IRES elements can be generated through the exchange of subdomain IRES fragments with their corresponding regions originating from a different virus species. Subdomain fragment chimeras that feature IRES elements in which only few nucleotides have been exchanged with the corresponding residues of a different virus species are described in Examples 6.

In principal, experimental procedures required to produce subdomain IRES chimeras are identical to those employed for the generation of domain IRES chimeras described above. PCR fragments generated from IRES element of the desired species origin are generated making use of cohesive ends created through the introduction of artificial endonuclease restriction sites following the parameters for maintenance of IRES function. Subsequently, IRES subdomain fragment chimeras can be produced through the ligation of different PCR products harboring engineered nucleotide exchanges with cohesive ends as described above.

The resulting intradomain hybrid IRES elements can be integrated into any poliovirus cDNA cloning cassette. Any IRES element, intact heterologous IRESes, domain chimeric IRESes, subdomain chimeric IRESes, or entirely non-viral or synthetic IRES elements can be integrated into the poliovirus cDNA cassette with great ease. For that purpose the cloning cassette is digested with the endonucleases flanking the IRES integration sites (nt #110, and nt #747) and the desired IRES elements featuring cohesive ends corresponding to those generated by endonuclease digestion of the cloning cassette is ligated into the cDNA.

Following these general instructions poliovirus recombinants can be generated using intact heterologous IRES elements, domain chimeric IRESes, or subdomain chimeric IRESes of a virus selected from the group of picornaviruses comprising poliovirus serotype 1–3, polioviruses (Sabin) serotype 1–3, Human Rhinovirus serotype 1–100, coxsackievirus serotype B1–B6, human echovirus serotype 1–7, 9, 11–27, 29–33, all having a 5'NTR region containing, an internal ribosomal entry site (IRES). Composite IRES elements can be integrated into a poliovirus selected from the group comprising PV serotype 1, serotype 2, and serotype 3, containing the coding sequences for structural proteins (P1), and for the non-structural proteins (P2 and P3) and a 3'NTR selected from the group consisting of wild type serotype 1, serotype 2, and serotype 3, wherein a. optionally, at least a part of P1 is substituted with the corresponding region of one of the viruses selected from the group consisting of PV1(S), PV2(S), and PV3(S)

b. optionally, at least a part of P3 is substituted with the corresponding region of one of the viruses selected from the group consisting of PV1(S), PV2(S), and PV3(S)

c. optionally, at least a part of the 3'NTR is substituted with the corresponding region of one of the viruses selected from the group consisting of PV1(S), PV2(S), and PV3(S).

Alternatively, the recombinant poliovirus maybe synthesized in vitro in accordance with the procedure described in Wimmer, et al., U.S. Pat. No. 5,674,729, incorporated herein by reference. The procedure is generally as follows.

Preparing a lysate from mammalian cells such as kidney cells, epithelial cells, liver cells, cells of the central nervous system, fibroblastic cells, transformed or tumorigenic cell lines thereof including HeLa cells, hepatoma cells and L cells; wherein the nuclei and mitochondria were removed; and the endogenous mRNA deactivated with micrococcal nuclease, calcium chloride and EGTA. The preparing of an in vitro synthesis medium by mixing: the lysate prepared above with the following materials to arrive at a final concentration in the mixture of about 1 mM ATP, about 20 $\mu$M to 1000 $\mu$M each of GTP, CTP and UTP, about 10 mM creatine phosphate, about 24 $\mu$g/mL creatine phosphokinase, about 2 mM dithiothreitol, about 24 $\mu$g/mL calf liver t-RNA, about 12 $\mu$M each of 20 amino acids, about 18 mM Herpes, pH 7.4, about 240 $\mu$M spermidine, about 50 mM to 200 mM potassium acetate, and about 1 mM to 4 mM of $MgCl_2$. Then adding isolated viral RNA from virus or in vitro synthesized viral RNA prepared from cDNA to the in vitro synthesis medium; and incubating the viral RNA for about 2 to 24 hrs. at a temperature from about 30° C. to 40° C.

Determination of Neuropathogenicity

The neuropathogenicity of poliovirus chimeras may be determined by following the standardized protocols of testing PV Sabin strains (oral PV vaccines). Generally, neurovirulence is determined in CD155-tg mice and Cynomolgus monkeys. CD155-tg mice were infected by either the intravenous (i.v.) or the intracerebral (i.c.) route and the clinical course of the ensuing neurological disease was monitored. Animal central nervous tissues were analyzed histopathologically and assayed for viral replication. Cynomolgus monkeys were inoculated intraspinally with $10^6$ $CCID_{50}$/mL (50% cell culture infectious doses/mL). Monkeys were sacrificed 17 days after intraspinal inoculation and the extent and distribution of spinal histopathology was assessed in a manner described by Omata, et al., *J. Virol.*, 58:348–358 (1986). Lesion scores were determined by established procedures. WHO Technical Report Series No. 80 (1990); Kawamura, N., et al., *J Virol.*, 63:1302–1309 (1989).

Assessment of the Oncolytic Properties

Oncolytic properties of the poliovirus chimeras of the invention were assessed by the in vitro growth of the chimeric viruses in a panel of cell lines derived from human malignancies. The procedure is described herebelow.

Cell lines originally obtained from surgical excised tumors and propagated in tissue culture are tested for susceptibility to oncolytic polioviruses in one-step growth curves as follows. Monolayer cell cultures (ca. $5 \times 10^6$ cells per plate) of the line in question are grown and infected at a multiplicity of infection (MOI) of 10. Infected cells are gently shaken for 30 min. at room temperature to allow for virus binding. Subsequently, cell monolayers are rinsed 5 times with 5 ml of serum-free medium each to remove unbound virus. Finally monolayers are overlaid with 2 ml of growth medium containing 2% of fetal calf serum and placed at 37° C. At defined time points (0, 2, 4, 6, 8, 10, 12, 24 hrs.) post infection (p.i.) cell culture dishes are frozen to stop the infectious process. At the completion of the experiment all collected samples are subjected to 4 consecutive freeze/thaw cycles to break open infected cells. The material thus treated is then analyzed with a plaque assay to determine the total amount of infectious virus present at each time point p.i. To this end serial dilutions of each sample are produced and used to infect HeLa cell monolayers that are overlaid with 3% Noble agar containing growth medium. The amount of infectious virus can be determined by counting the plaques of infected and lysed cells that formed underneath the solidified agar corresponding to the number of infectious particles present within the sample. The quantity of infectious particles at various time points is plotted against time post infection (p.i.). The growth curve thus obtained represents an accurate reflection of the replication and hence oncolytic capacity of the virus strain tested in that particular cell line.

The oncolytic properties of the poliovirus chimeras of the present invention may also be assessed in vivo as follows.

Experimental tumors are produced in athymic mice by subcutaneous or stereotactic intracerebral implantation of malignant cells. Tumor progression in untreated athymic mice and athymic mice that have been administered oncolytic poliovirus recombinants following various treatment regimens are followed by clinical observation and pathological examination. The technique of tumor implantation into athymic mice is standard procedure described in detail in Fogh,.J., et al., *J. Natl. Cancer Inst.*, 59:221–226 (1977).

Pharmaceutical Compositions and Treatment Methods

The poliovirus chimeras of this invention are useful in prophylactic and therapeutic compositions for treating malignant tumors in various organs, such as: breast, colon, bronchial passage, epithelial lining of the gastrointestinal, upper respiratory and genito-urinary tracts, liver, prostate and the brain.

The most preferred pharmaceutical compositions of this invention for administration to humans comprise the poliovirus chimeras, PV1(RIPO) and PV1(RIPOS).

The pharmaceutical compositions of this invention may further comprise other therapeutics for the prophylaxis of malignant tumors. For example, the poliovirus chimeras of this invention may be used in combination with surgery, radiation therapy and/or chemotherapy. Furthermore, one or more poliovirus chimeras may be used in combination with two or more of the foregoing therapeutic procedures. Such combination therapies may advantageously utilize lower dosages of the administered therapeutic agents, thus avoiding possible toxicities or adverse effects associated with the various monotherapies.

The pharmaceutical compositions of this invention comprise a therapeutically effective amount of one or more poliovirus chimeras according to this invention, and a pharmaceutically acceptable carrier. By "therapeutically effective amount" is meant an amount capable of causing lysis of the cancer cells to cause tumor necrosis. By "pharmaceutically acceptable carrier" is meant a carrier that does not cause an allergic reaction or other untoward effect in patients to whom it is administered.

Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the poliovirus chimeras.

The compositions of this invention may be in a variety of forms. These include, for example, liquid dosage forms, such as liquid solutions, dispersions or suspensions, injectable and infusible solutions. The preferred form depends on the intended mode of administration and prophylactic or therapeutic application. The preferred compositions are in the form of injectable or infusible solutions.

Therapeutic oncolytic polioviruses can be delivered intravenously, intrathecally or intraneoplastically (directly into the primary tumor). The preferred mode of administration is directly to the tumor site. For all forms of delivery, the recombinant virus is most preferably formulated in a physiological salt solution: e.g. HANKS balanced 'salt solution [composition: 1.3 mM $CaCl_2$ (anhyd.), 5.0 mM KCl, 0.3 mM $KH_2PO_4$, 0.5 mM $MgCl_2.6H_2O$, 0.4 mM $MgSO_4.7H_2O$, 138 mM NaCl, 4.0 mM $NaHCO_3$, 0.3 mM $Na_2HPO_4$, 5.6 mM D-Glucose]. The inoculum of virus applied for therapeutic purposes can be administered in an exceedingly small volume ranging between 1–10 μl. Recombinant polioviruses stored in a physiological salt solution of the composition detailed above can be stored at −80° C. for many years with minimal loss of activity. Short term storage should be at 4° C. At this temperature virus solutions can be stored for at least one year with minimal loss of activity.

It will be apparent to those of skill in the art that the therapeutically effective amount of poliovirus chimeras of this invention will depend upon the administration schedule, the unit dose of poliovirus chimeras administered, whether the poliovirus chimera is administered in combination with other therapeutic agents, the status and health of the patient.

The therapeutically effective amounts of oncolytic recombinant virus can be determined empirically and depend on the maximal amount of the recombinant virus that can be administered safely, and the minimal amount of the recombinant virus that produces efficient oncolysis. Experiments studying the effect of intraspinal inoculation of candidate oncolytic polioviruses into non-human primates (FIG. 3) indicate that a dose of $5\times10^6$ pfu of PV1(RIPO) or PV1 (RIPOS) can be used for intracerebral, intraspinal or intrathecal administration without the danger of inducing any neurological sequelae. Based on the Cynomolgus monkey data, weighing just about 7.0 pounds, the appropriate dose for an average human (e.g. 140 pounds) is about $1\times10^8$ pfu of virus. Maximal virus delivery appeared to be beneficial to achieve maximal oncolysis in animal experiments. Thus, the virus inoculums used for intraneoplastic injections into humans would be in the range of $1\times10^6$ to $5\times10^8$ pfu. However, the dose may be adjusted in accordance with the particular recombinant poliovirus contemplated and the route of administration desired.

Intraneoplastic inoculations of oncolytic polioviruses produced significantly better oncolysis rates than intravenous administration in experimental animals (FIG. 20). Based on the data obtained, the recombinant polioviruses of the present invention are non-neurovirulent and non-pathogenic. The mechanism by which, oncolysis takes place is by the ability of these recombinant polioviruses to replicate in the cancer cells at a rate which causes the cells to "explode". The recombinant polioviruses of the present invention do not affect normal cellular processes and are thus not expected to be toxic to normal cells. Therefore, it would appear that there is no upper limit to the dose level which can be administered. Thus, to produce the same oncolytic effect achieved through intraneoplastic inoculation of virus by the intravenous route, significantly higher amounts of virus should be and could be administered. However, in an abundance of caution, the appropriate dose level should be the minimum amount which would achieve the oncolytic effect.

Therapeutic inoculations of oncolytic polioviruses can be given repeatedly, depending upon the effect of the initial treatment regimen. Since poliovirus exists in three antigenically distinct serotypes, candidate oncolytic polioviruses, e.g. PV1(RIPO), will be available as three different serotypes, e.g. PV1(RIPO), PV2(RIPO), PV3(RIPO). Should the host's immune response to a particular oncolytic poliovirus administered initially limit its effectiveness, additional injections of an oncolytic poliovirus with a different poliovirus serotype can be made. The host's immune response to a particular poliovirus can be easily determined serologically. It will be recognized, however, that lower or higher dosages than those indicated above according to the administration schedules selected.

For that purpose, serological data on the status of immunity against any given poliovirus can be used to make an informed decision on which variant of the oncolytic poliovirus to be used. For example, if a high titer against poliovirus serotype 1 is evident through serological analysis of a candidate patient for treatment with ancolytic nonpathogenic polioviruses, a serotype 2 or –3 variant of the theraupeutic virus perparation should be used for tumor therapy.

In order that this invention may be better understood, the following examples are set forth. These examples are for purposes of illustration only, and are not to be construed as limiting the scope of the invention.

EXAMPLE 1

Construction of Intergeneric PV Recombinants
Construction of PV1(RIPO)/3DS/3'S

The construction of a prototype recombinant poliovirus PV1(RIPOS) was described in Gromeier, M., et al., *Proc. Natl. Acad. Sci. USA*. 91:1406–1410 (1996), incorporated herein by reference.

PV1(RIPOS/3DS/3'S), having a genome of PV1(M) with a 5'NTR region containing an IRES derived from H (b) optionally, at least a part of P1 is substituted with the corresponding region of one of the viruses selected from the group consisting of PV1(S), PV2(S), and PV3(S)

(c) optionally, at least a part of P3 substituted with the corresponding region of one of the viruses selected from the group consisting of PV1(S), PV2(S), and PV3(S)

(d) optionally, at least a part of the 3'NTR substituted with the corresponding region of one of the viruses selected from the group consisting of PV1(S), PV2(S), and PV3(S).

Furthermore, experiments involving virus recombinants carrying composite IRES elements composed out of domains II, III, IV, V, and VI derived from divergent virus species are described. The cloning procedures for a number of exemplifying intergeneric IRES domain recombinants (displayed in FIG. 5) are as follows.

Construct PV1(R2–4) was generated by ligating a PCR product encompassing the HRV2 IRES domains II–IV using primers (SEQ ID NO:1) and 5'-CCGGATCCAAAGCGAGCACACGGGGC-3' (SEQ ID NO:17) to a PCR product encompassing PV1(M) domains V and VI produced with primers 5'-CCGGATCCTCCGGCCCCTGAATGCG-3' (SEQ ID NO:18) and 5'-CCTGAGCTCCCATTATGATACAATTGTCTG-3' (SEQ ID NO:19).

For construct PV1(R2–4, 6), primers (SEQ ID NO:1) and (SEQ ID NO:17) were used to generate a PCR fragment encompassing domains II–IV of the HRV2 IRES which was ligated to a PCR fragment obtained from PV1(M) using primers (SEQ ID NO:18) and 5'-GGTACCAATAAAATAAAAGGAAACACGGACACC-3' (SEQ ID NO:20) corresponding to PV1(M) domain V and to the PCR product from HRV2 yielding domain VI with the use of primers 5'-GCGGTACCGCTTATGGTGACAATATATAC-3' (SEQ ID NO:21) and (SEQ ID NO:2).

For construct PV1(R2–5) primers (SEQ ID NO:1) and 5'-CCGGTACCTAAAGGAAAAAGTGAAACA-3' (SEQ ID NO:22) were used to generate a fragment containing domains II–V of HRV2 that was ligated to domain VI of PV1(M), PCR synthesized with the use of primers 5'-CCGGTACCGCTTATGGTGACAATCACAG-3' (SEQ ID NO:23) and (SEQ ID NO:19). Construct PV1(R5–6) was generated by ligating a PCR product from PV1(M) using primers 5'-GGGAATTCAGACGCACAAAACCAAG-3' (SEQ ID NO:24) and 5'-CCGGATCCTTATGTAGCTCAATAGG-3' (SEQ ID NO:25) with a PCR product encompassing domains V and VI from HRV2 generated with primers 5'-CCGGATCCTCCGGCCCCTGAATGTGG-3' (SEQ ID NO:26) and (SEQ ID NO:2).

Construct PV1(R5) was generated ligating a PCR product spanning PV1(M) domains II–IV produced with primers (SEQ ID NO:23) and (SEQ ID NO:24) to a PCR product encompassing domain V of HRV2 generated with primers (SEQ ID NO:26) and (SEQ ID NO:22) and a PCR product representing domain VI of PV1(M) produced with primers (SEQ ID NO:23) and (SEQ ID NO:19). PV1(R6) was the result of ligating a PCR product from a reaction using primers (SEQ ID NO:24) and (SEQ ID NO:20) corresponding to IRES domain II–V of PV1(M) to a PCR product generated with the use of primers (SEQ ID NO:21) and (SEQ ID NO:2) corresponding to HRV2 IRES domain VI.

Recombinant IRES elements combining IRES domains from different picornavirus species can be generated using fragments of the IRES elements of a virus selected from the group of picornaviruses comprising poliovirus serotype 1–3, polioviruses (Sabin) serotype 1–3, Human Rhinovirus serotype 1–100, coxsackievirus serotype B1–B6, human echovirus serotype 1–7, 9, 11–27, 29–33, all having a 5'NTR region containing an internal ribosomal entry site (IRES).

Composite IRES elements can be integrated into a poliovirus selected from the group comprising PV serotype 1, serotype 2, and serotype 3, containing the coding sequences for structural proteins (P1), and for the non-structural proteins (P2 and P3) and a 3'NTR selected from the group consisting of wild type serotype 1, serotype 2, and serotype 3.

Optionally, at least a part of p1 is substituted with the corresponding region of one of the viruses selected from the group consisting of PV1(S), PV2(S), and PV3(S); or at least a part of P3 is substituted with the corresponding region of one of the viruses selected from the group consisting of PV1(S), PV2(S), and PV3(S); or, at least a part of the 3'NTR is substituted with the corresponding region of one of the viruses selected from the group consisting of PV1(S), PV2 (S), and PV3(S).

Plasmids containing the cDNA of the resulting recombinant virus of the above mentioned genotype or any other variant were amplified, purified and digested with the restriction endonuclease FspI for linearization (this endonuclease cuts within vectorial sequences). The resulting linearized cDNA (which contains a recognition motif for the DNA-dependent RNA polymerase T7 preceding the 5' insertion site of the virus cDNA) was used for in vitro transcription using T7 polymerase to produce full-length viral RNA. Viral RNA thus generated was used to transfect HeLa cells by the Dextran-sulfate method in order to produce infectious virus. Transfected cells were observed for the occurrence of the cytopathic effect indicating productive poliovirus infection and infectious virus will be propagated in HeLa cells, purified and frozen for indefinite storage.

EXAMPLE 2

In Vitro Growth of PV Recombinants in Cultured Cells to Determine Neurovirulence Neurovirulence is tested in vitro and in vivo. For in vitro testing, cell lines HEp-2, derived from a human laryngeal epidermoid carcinoma, and SK-N-MC, derived from a neuroblastoma in a human subject, were obtained from ATCC and grown in Dulbecco's minimal essential medium (DMEM; GIBCO). 10% fetal bovine serum (GIBCO), penicillin (100 units/mL) and streptomycin (100 $\mu$g/mL). HEp-2 and SK-N-MC, and monolayers in 6 cm. plastic culture dishes were inoculated with a suspension of PV1(RIPO) or PV1(RIPOS) at a multiplicity of infection of 10 and gently shaken for 30 min. at room temperature. Afterwards, the dishes were washed five times each with 5 mL of DMEM. Then the monolayers were overlaid with 2 mL of DMEM containing 2% fetal bovine serum. Synchronized infection was interrupted at the indicated intervals, cell monolayers were lysed by four consecutive freeze-thaw cycles, and the viral yield in the cell lysate was determined in a plaque assay.

The attenuated phenotype of poliovirus has been documented to be reproducible in tissue culture. Agol, V. I., et al., *J. Virol.*, 63:4034–4038 (1989). La Monica, N. & Racaniello, V. R., *J. Virol.*, 63:2357–2360 (1989). Growth defects of attenuated strains of poliovirus evident in SK-N-MC neuroblastoma cell lines correlated with the deficiency to cause poliomyelitic disease in Cynomolgus monkeys or CD155 tg mice. Thus, the non-neuropathogenic phenotype, a prerequisite for the engineering of safe oncolytic polioviruses devoid of unwanted pathogenic properties, can be ascertained with great ease and accuracy by establishing one-step growth curves in SK-N-MC neuroblastoma cells as described above.

The results are presented in FIGS. 3–6 and show that neurovirulence or neuropathogenicity has been ablated in PV1(RIPO) and PV1(RIPOS). The non-neuropathogenic phenotype has been demonstrated for a great number of different recombinant IRES constructs described in this application. These include polioviruses whose IRES elements have been entirely (FIG. 4) or in part (FIGS. 6, 8) substituted with the corresponding entire IRES elements or partial IRES fragments derived from various rhinoviruses (HRV2, HRV14), Coxsackie B virus (CBV4), and Echovirus (E9).

EXAMPLE 3

Determination of Neurovirulence in CD155-tg Mice and Cynomolgus Monkeys

All PV strains containing either the homologous or the heterologous IRES elements were assayed to determine their neurovirulent potential in mice transgenic for the human PV receptor, CD155-tg mice strain ICR.PVR.tgI, Koike et al., supra. Wild type (wt) PV strains induce in these animals a neurological disease indistinguishable, clinically and histologically, from primate poliomyelitis. CD155-tg mice were infected either by the i.c. or i.v. route and the clinical course of ensuing neurological disease was monitored. Animal central nervous system tissues were analyzed histopathologically and assayed for viral replication.

Groups of four mice were infected with a given amount of virus ranging from $10^2$ to $10^4$ pfu i.c. and $10^3$ to $10^5$ pfu i.v. for PV1(M) and PV1(R2–4); $10^5$ to $10^8$ i.v. and $10^7$ to $10^9$ i.c. for PV1(S), PV1(RIPO), PV1(RIPOS), PV1(R2–5), PV1 (R6), PV1(R2–4,6), PV1(R5). CD155 tg mice that were inoculated with the various constructs were clinically observed and fatalities were recorded. $LD_{50}$ values were calculated by the method of Reed and Muench, *Am. J. Hyg.*, 27:493–495 (1938).

Remarkably, PV1(RIPO) and PV1(RIPOS) were devoid of any neurovirulent potential and produced only a transient subtle paraparesis in CD155 tg mice. Intracerebral injections with PV1(RIPO) or PV1(RIPOS) up to $10^9$ pfu did not cause any apparent alterations within the central nervous system, and intraspinal replication of these recombinants was absent.

EXAMPLE 4

Determination of Oncolysis with PV Chimeras

PV1(RIPO) was constructed by exchanging the cognate PV IRES with that of HRV2 (See FIG. 5). PV1(RIPO) is exceptional because of its loss of pathogenicity in CD155-tg mice, which develop poliomyelitis upon poliovirus infection, Ren, et al., supra; Koike et al., supra; Gromeier et al., supra) and in non-human primates (Cynomolgus monkeys) after intraspinal inoculation (FIG. 3).

Loss of neuropathogenicity of PV1(RIPO) was also evident by poor propagation in cultured cell lines of neuronal derivation, a phenomenon that correlates with cell-internal restriction of replication (FIG. 4). In contrast, propagation of PV1(RIPO) in rapidly dividing malignant cells, such as HTB-14 or HTB-15 glioblastoma cells (FIG. 9) or in HeLa cells (FIG. 8) was near wild type levels. The locus of attenuation of PV1(RIPO) was mapped to two stem-loop domains within the HRV2 IRES. See FIG. 5, which depicts PV variants with PV/HRV2 chimeric IRESes where HRV2 IRES components are boxed. The combined IRES domains V/VI of PV were required for the neuropathogenic phenotype, because only wild type PV1(M) and chimera PV1(R2–4) caused poliomyelitis in CD155-tg mice. See right column which indicates neuropathogenicity indices. PV1(RIPOS) that carries the P1 capsid encoding region of the live attenuated vaccine strain PV1(Sabin) have also been constructed.

The oncolytic potential of recombinant polioviruses was assessed in tissue culture by the establishment of one-step growth curves in tissue culture cell lines derived from excised human tumors. To that end, cultured cells monolayer were grown and infected with the oncolytic poliovirus recombinant in question. Infection was interrupted at predetermined intervals and a one-step growth curve was established following the procedures outlined one herein above under assessment of oncolytic properties.

Oncolytic potential of PV1(RIPO) has been determined by analysis of growth kinetics in cell culture for a large number of malignant cell types originating from various source neoplasms. PV1(RIPO) unfolded oncolytic activity in cell culture against HTB-14 and HTB-15 (FIG. 9), SF-767, SF-763, SF-295, and SF-188 glioblastoma cell lines (FIG. 10), HTB-185 medulloblastoma cell line (FIG. 11), CRL-7721 mammary carcinoma cell line (FIG. 12), CRL-1435 and HTB-81 prostate carcinoma cell lines (FIG. 13), CCL-230 colon carcinoma cell line (FIG. 14), Hep-G2 and HuH7 hepatocellular carcinoma cell lines (FIG. 15), CRL-2195 bronchial carcinoma cell line (FIG. 16), and HEp-2 and HTB-32 epidermoid carcinoma cell lines (FIG. 17). The growth characteristics of PV1(RIPO) in this panel of malignant cell lines is representative for all PV/HRV2 IRES chimeras described in this application (data not shown).

EXAMPLE 5

Oncolysis of Astrocytomas with Chimeric Polioviruses

Using the astrocytoma cell lines HTB-14 and HTB-15 (obtained from ATCC), malignant gliomas were established through subcutaneous (HTB-15) and intracerebral (HTB-14) implantation of cells into nude mice. Thirty days after inoculation of $5\times10^6$ tumor cells into both subaxillary folds of Cr:(NCr)-nufBR homozygotic nude mice, 70% of treated mice developed bilateral tumor growths that exceeded 6 mm in diameter. A group of 4 mice with bilateral subcutaneous growths of at least 6 mm diameter was treated by monolateral intraneoplastic inoculation of $10^8$ plaque forming units (pfu) of PV1(RIPO). Tumor progression in the virus-treated group or untreated controls, was followed clinically as well as pathologically. Whereas, tumor growth in untreated mice proceeded at a steady rate, yielding tumors above 9 mm diameter at 60 days post implantation, malignant growths in the treated group receded dramatically. FIGS. 18A, 18C, and 18E show tumor tissue from an untreated animal; FIGS. 18B, 18D, and 18F show a receding neoplasm from a virus-injected mouse. Drastic shrinkage of tumor mass occurred upon virus treatment (FIG. 18B) resulting in the formation of a wall of necrotic debris surrounding remaining tumor (FIG. 18D) that is being infiltrated by invading macrophages (FIG. 18F). After 14 days, tumors in virus-treated mice could no longer be recognized by macroscopic observation. Tumor recession was not limited to the neoplasm treated with intraneoplastic virus inoculation but also led to disappearance of the contralateral growth as judged by pathological analysis. Observations indicate that hematogenous spread of virus occurs after intraneoplastic inoculation and releases amounts of virus sufficient to infect and destroy tumors at distant sites.

Figure 19:
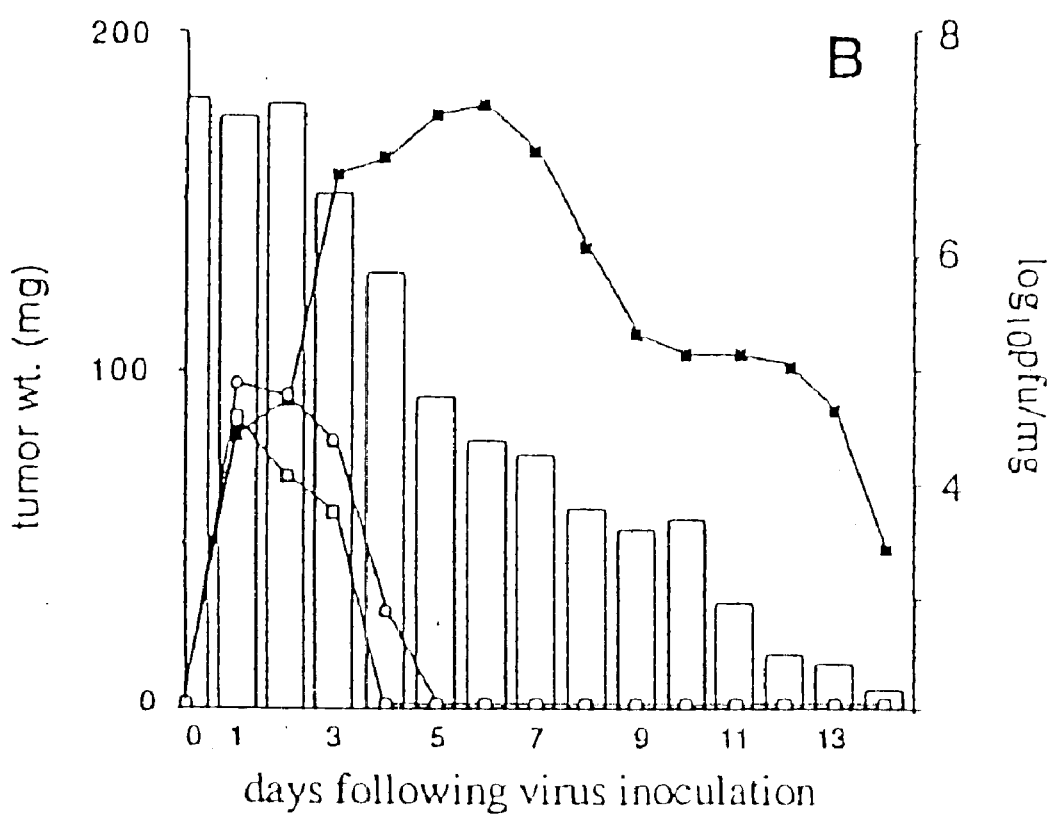
FIG. 19 is a graphic representation of the replication kinetics and tumor necrosis induced by PV1(RIPO) after intraneoplastic inoculation into tumors derived from cell line HTB-15 implanted subcutaneously into athymic mice. Athymic mice carrying subcutaneous gliomas received a single intravenous inoculation of $5 \times 10^7$ PV1(RIPO) 30 days after tumor implantation. The graph shows solid viral replication within neoplastic tissue with rapid and drastic tumor shrinkage as compared with the absence of virus propagation in liver (open circles) and brain (open squares). After 14 days the tumor was no longer macroscopically visible, precluding tumor isolation and determination of weight.

The observation that i.v. administration of virus was sufficient for maximal oncolysis was confirmed as follows: mice harboring growing tumors (>8 mm diameter) were infected iv with 5×10$^7$ pfu PV1(RIPO). Tumor regress was assessed by weighing tumors in individual mice, sacrificed each consecutive day following virus inoculation. See FIG. 19, wherein, grey bars indicate tumor weight, and intraneoplastic and extratumoral virus replication is indicated by superimposed graphs. Tumors were homogenized and the viral load was determined in a plaque assay. Drastic reduction in tumor size was accompanied by high levels of virus replication within the receding neoplasm. Treatment of intracerebral gliomas with PV1(RIPO) led to tumor regress and remission. Mice received stereotactic intracerebral implants of 5×10$^4$ HTB-14 cells.

Figure 20A:
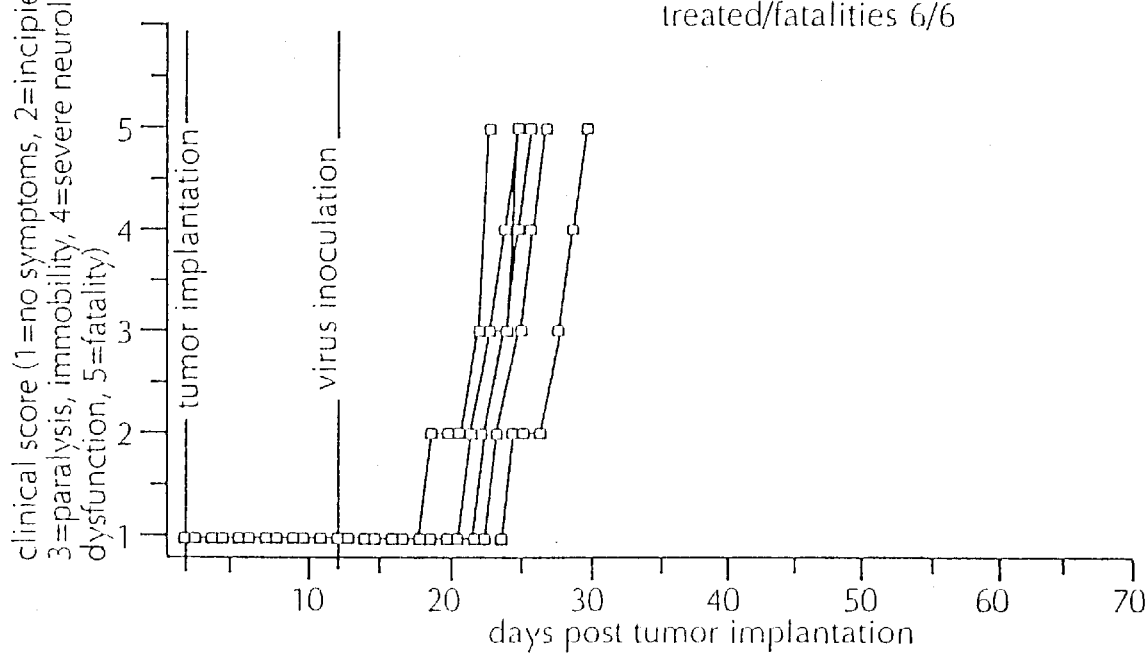
FIGS. 20A–20D show the progression of neurological disease in athymic mice implanted with HTB-14 and harboring intracerebral glioblastomas (FIG. 20A) and the result of treatment with PV1(RIPO) administered via various routes. The graphs represent the progression of clinically apparent neurological symptoms stemming from expanding hemispheric neoplasms. The ratio of surviving/affected animals and the average survival is indicated.
Figure 20B:
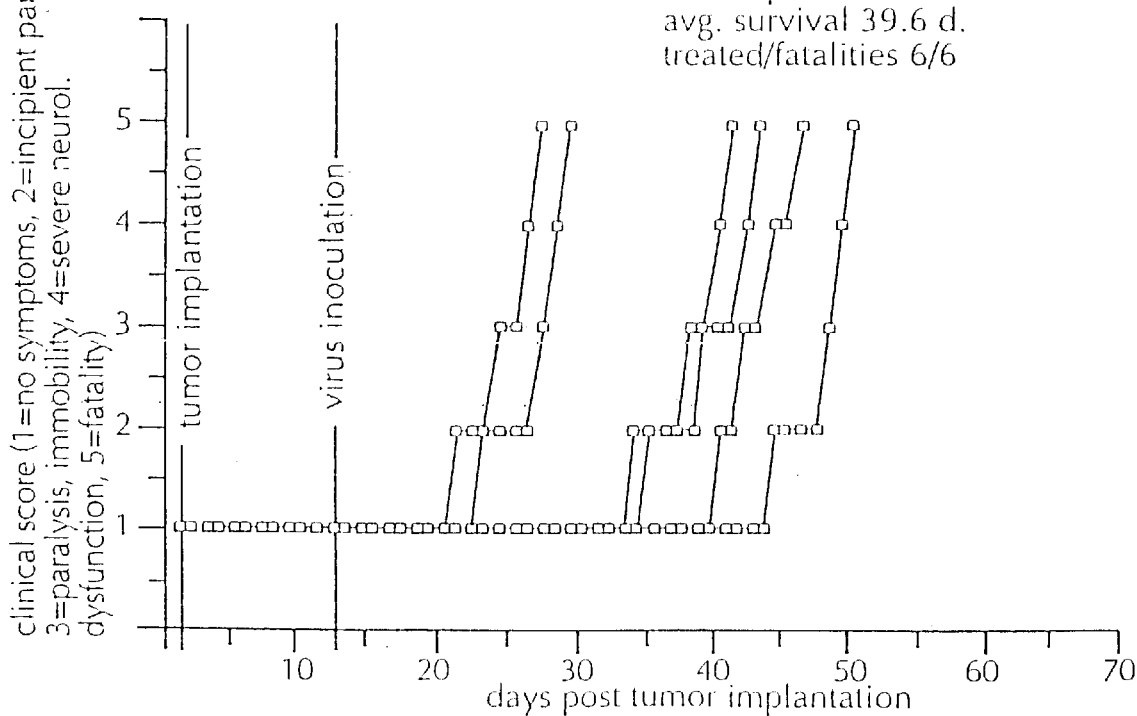
Figure 20C:
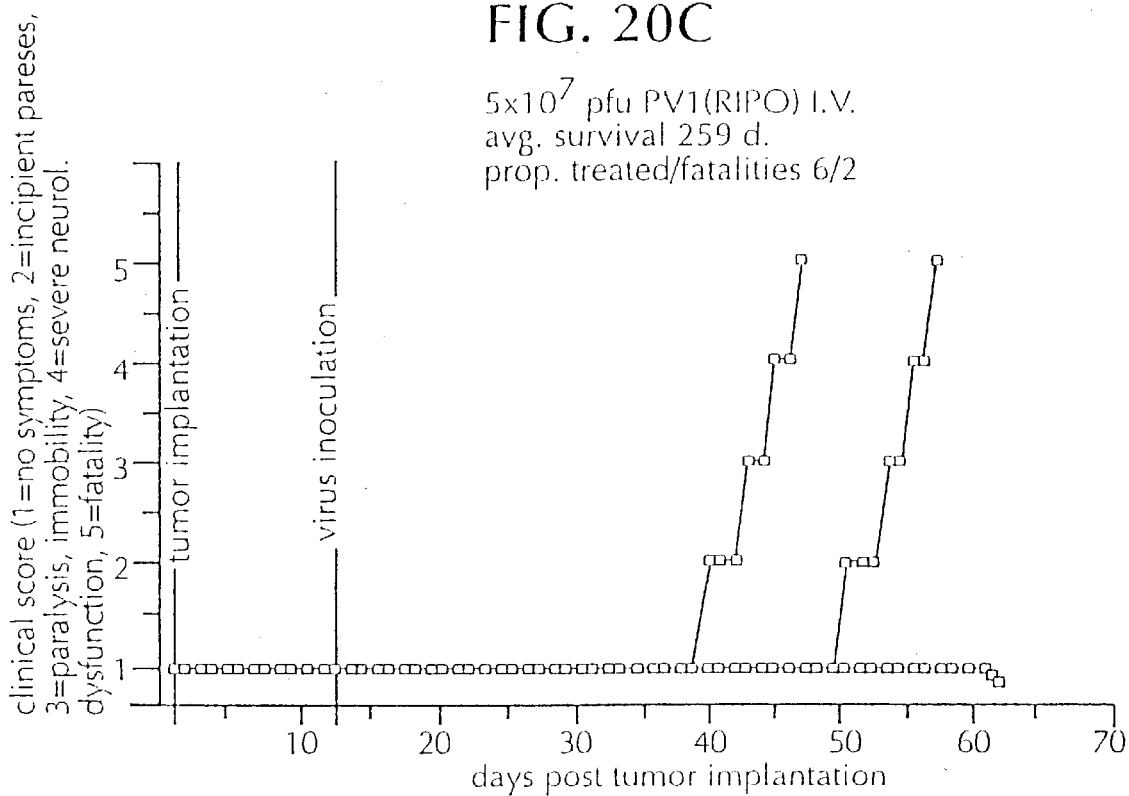
Figure 20D:
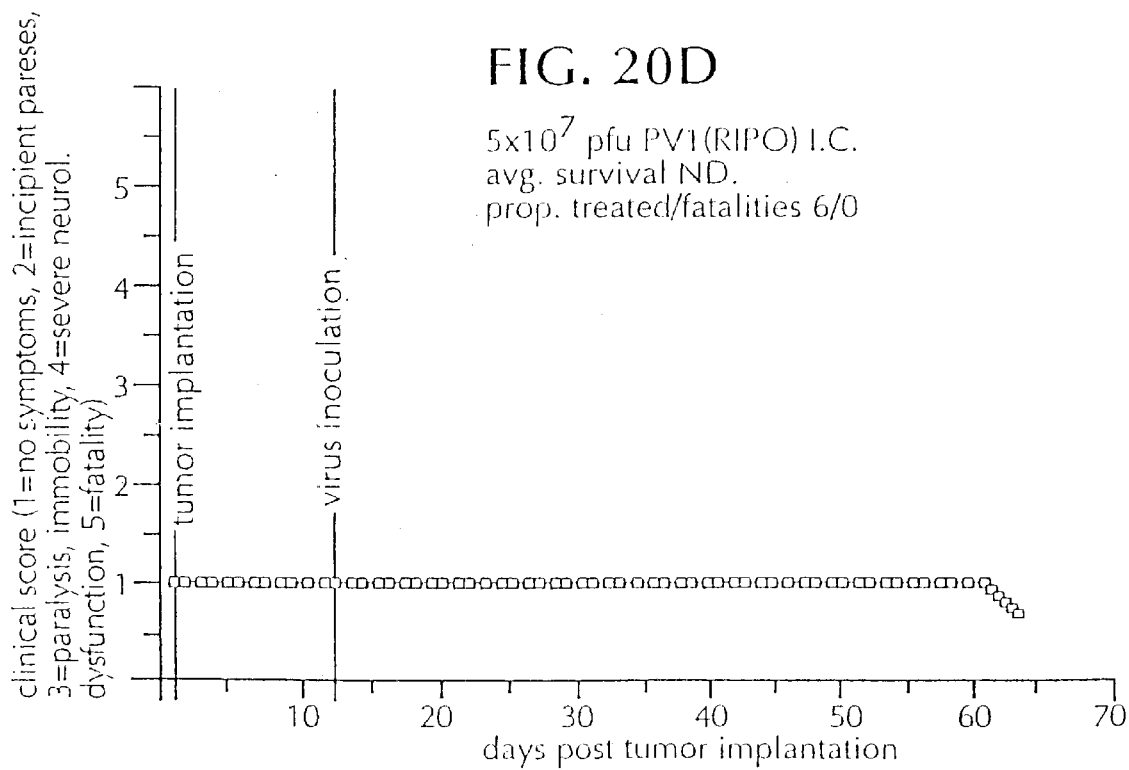

Four groups, each comprising six mice harboring intracerebral gliomas, were formed. Group 1 was left untreated, group 2 received a single intramuscular (i.m.) inoculation of 5×10$^7$ pfu PV1(RIPO), group 3 was administered a single intravenous (i.v.) inoculation of 5×10$^7$ pfu PV1(RIPO), and group 4 received 5×10$^7$ pfu PV1(RIPO) intracerebrally (i.c.). As can be seen in FIG. 20A, untreated mice succumbed to neurological complications stemming from the expanding intrahemispheric neoplasm 21–29 days following tumor implantation (average survival was 26 days following tumor implantation). Mice treated with an i.m. inoculation of PV1(RIPO) had a slightly elevated life expectancy (average 40 days). In contrast, mice that had received i.v. inoculation of PV1(RIPO) had a significantly improved outcome of neoplastic disease (only 2 out of 6 mice died in consequence to tumor implantation; FIG. 20C). Mice treated with a single i.c. inoculation of PV1(RIPO) were completely protected against malignant glioma (none of the treated mice succumbed to their malignancy).

Figure 21A:
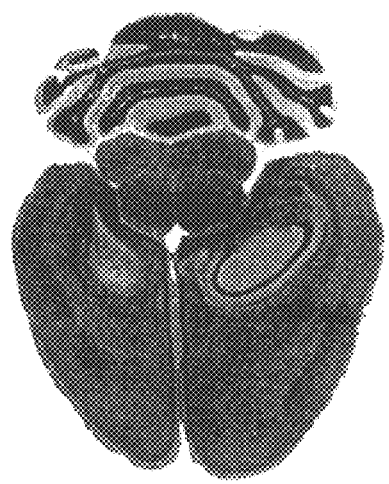
FIGS. 21A–21D are brain sections of: normal control athymic mice (FIGS. 21A and 21B), untreated athymic mice harboring intraventricular implanted gliomas, cell line HTb-14 (FIGS. 21C–21D) and athymic mice harboring intraventricular implanted gliomas that had received a single intracerebral inoculation of PV1(RIPO) 12 days following tumor implantation (FIG. 21E).
Figure 21B:
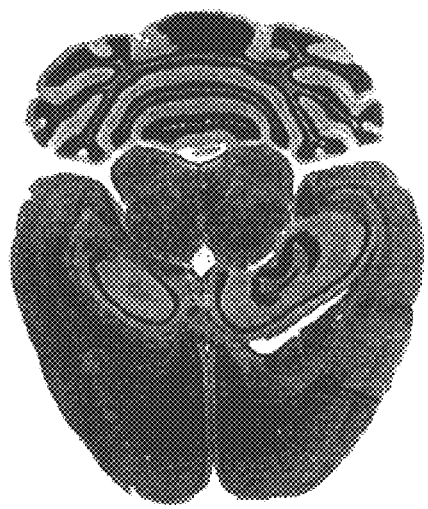
Figure 21C:
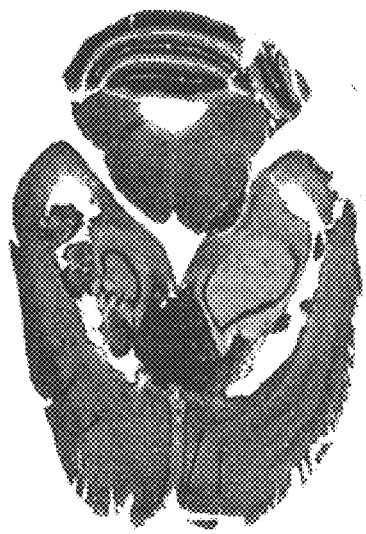
Figure 21D:
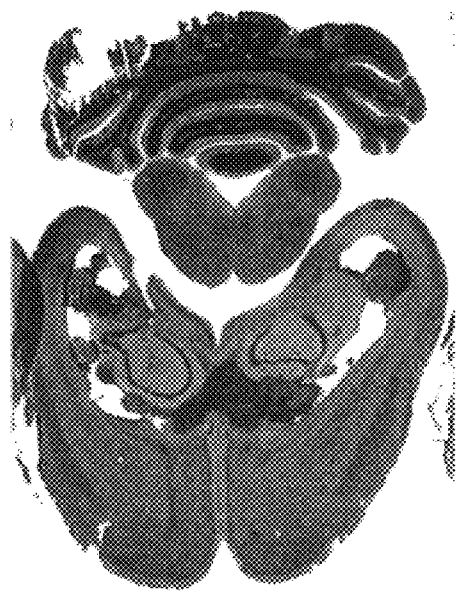
Figure 21E:
FIG. 21E shows the dramatic reduction of tumor mass. A tissue defect stemming from destruction of a paraventricular neoplastic lesion adherent to the lateral wall of the right ventricle is clearly visible (for details see FIG. 22).

Occasionally, the athymic mice treated with an i.c. inoculation of PV1(RIPO) 12 days after tumor implantation experienced the emergence of neurological symptoms in a period of 15–21 days post tumor implantation (3–9 days following virus administration). However, even severe symptoms of neurological dysfunction in these i.c. treated mice improved within 1 week of virus administration. Most astonishingly, all treated mice experienced complete recovery from their symptoms. Pathological analysis revealed that gliomas in untreated mice had grown to sizeable proportions accounting for the fatal outcome. See FIGS. 21A–21E. FIGS. 21C and 21D show rapidly expanding tumor masses distributed within the lateral ventricles; FIGS. 21A and 21B show control sections from healthy mice. In contrast, FIG. 21E shows that gliomas in treated mice underwent drastic shrinkage and eventual remission. In FIG. 21E a brain section, obtained from an animal treated with PV1(RIPO) 14 days after tumor implantation, shows the remnant of an implanted glioma leaving a tissue defect within brain parenchyma bordering the left lateral ventricle.

FIGS. 22A to 22C show details from brain sections in FIG. 21. A control section (FIG. 22A) shows the normal lateral ventricle with its intact ependymal lining. FIG. 22B clearly shows a section through the brain of an untreated mouse with tumor implant with a circular tumor mass infiltrating the adjacent parenchyma. FIG. 22C shows a section of the brain of a virus-treated mouse with tumor implant. Macrophagic infiltrates indicate removal of remaining debris stemming from an intraventricular neoplasm destroyed by PV1(RIPO).

EXAMPLE 6

Construction of PV1(prr)

An example for the construction of similar intradomain IRES chimeras is given for the generation of PV1(prr). PV1(prr) was produced by ligating a PCR product corresponding to PV1(M) IRES domains II–V (ascending loop) with the upper loop region of domain V (nt #492–508) of HRV2 using primers (SEQ ID NO:24) and 5'-GGTTACGTGCTCTAGCTCCGAGGTTGGG-3' (SEQ ID NO:27) to a PCR fragment encompassing PV1(M) domain V (descending loop) using primers 5'-AGAGCACGTAACCCAATGTGTATCTAGTCGTAA CGCGCAACTCC-3' (SEQ ID NO:28) and (SEQ ID NO:20) and a PCR fragment corresponding to PV1(M) domain VI with the upper loop region (nt #582–609) of HRV2 using primers (SEQ ID NO:21) and (SEQ ID NO:2).

Recombinant IRES elements of various composition can be cloned into the PV1(RIPO) cloning cassette and used to produce chimeric viruses by the methods described above.

PV1(ppr) may be genotypically represented as: 5'cloverleaf (PV1)—IRES nt #106–484 (PV1)—IRES nt #484–508 (HRV2)—IRES nt #508–593 PV1)—IRES nt #594–612 (HRV2)—P1 [optionally derived from PV1/PV2/PV3or PV1(S)/PV2(S)/PV3(S)]—P2 (PV1)—P3 excl. 3D$^{pol}$ (nt #5111–5986; PV1) 3D$^{pol}$ [nt #5987–7369; PV1(S)]—3'NTR [optionally derived from PV1/PV2/PV3 or PV1(S)/PV2(S)/PV3(S)]—poly(A) (PV1).

The nonpathogenic phenotype for PV1(prr) has been confirmed in one-step growth curves in SK-N-MC neuroblastoma cells (FIG. 8) and in CD155 tg mice (FIG. 8). Furthermore, PV1(prr) shares the oncolytic potential of PV1(RIPO) in the panel of malignant cell lines described on pg. 48–49. Thus, the phenotypical hallmarks of PV1(RIPO) and PV1(RIPOS), lack of neuropathogenicity in cell culture and experimental animals with oncolytic potential against cultured malignant cell types, are also associated with PV1 (prr).

What we claim are:

1. A recombinant poliovirus constructed from a poliovirus having a 5'NTR containing an internal ribosomal entry site (IRES), and the coding sequences for structural proteins (P1), and for the non-structural proteins (P2 and P3) and a 3'NTR selected from the group consisting of wild type serotype 1, serotype 2, and serotype 3, wherein
  a. i. a part of the IRES, at least 19 nucleotides, of the poliovirus is substituted with a part of the IRES, at least 19 nucleotides, of Human Rhinovirus also having a 5'NTR region containing an internal ribosomal entry site (IRES), the coding sequences of structural proteins (P1) and for the non-structural proteins (P2 and P3) and a 3'NTR, or
     ii. a part of the IRES, at least 19 nucleotides, of the poliovirus is substituted with a part of the IRES, at least 19 nucleotides, of a virus selected from the group of picornaviruses comprising Human Rhinovirus serotype 1, 3–100, coxsackievirus serotype B1–B6, human echovirus serotype 1–7, 11–27, and 29–33, also having a 5'NTR region containing an internal ribosomal entry site (IRES), the coding sequences of structural proteins (P1), and for the non-structural proteins (P2 and P3) and 3'NTR, and wherein
  b. optionally, P1 of the poliovirus is substituted with P1 of a Poliovirus (Sabin), selected from the groups consisting of PV1(S), PV2(S) and PV3(S);
  c. optionally, at least $3D^{pol}$ of P3 of the poliovirus is substituted with at least $3D^{pol}$ of P3 of a Poliovirus (Sabin), selected from the groups consisting of PV1(S), PV2(S) and PV3(S); and
  d. optionally, 3'NTR of the poliovirus is substituted with the 3'NTR of a Poliovirus (Sabin), selected from the group consisting of PV1(S), PV2(S), PV3(S).

2. A composition comprising a recombinant poliovirus according to claim 1 and a pharmaceutically acceptable carrier.

3. A recombinant poliovirus according to claim 1 wherein, a part of the IRES, at least 19 nucleotides, of the poliovirus is substituted with a part of the IRES, at least 19 nucleotides, of the Human Rhinovirus serotype 2.

4. A composition comprising a recombinant poliovirus according to claim 3 and a pharmaceutically acceptable carrier.

5. A recombinant poliovirus according to claim 3 PV1 (R2–4,6), wherein the poliovirus is PV1(M) and the IRES domains II, III, IV and VI are substituted with the IRES domains II, III, IV and VI of the Human Rhinovirus serotype 2.

6. A composition comprising a recombinant poliovirus according to claim 5 and a pharmaceutically acceptable carrier.

7. A recombinant poliovirus according to claim 3, PV1 (R5), wherein the poliovirus is PV1(M) and the IRES domain V is substituted with the IRES domain V of the Human Rhinovirus serotype 2.

8. A composition comprising a recombinant poliovirus according to claim 7 and a pharmaceutically acceptable carrier.

9. A recombinant poliovirus according to claim 3 PV1 (R2–5), wherein the poliovirus is PV1(M) and the IRES domains II, III, IV and V is substituted with the IRES domains II, III, IV and V of the Human Rhinovirus serotype 2.

10. A composition comprising a recombinant poliovirus according to claim 9 and a pharmaceutically acceptable carrier.

11. A recombinant poliovirus according to claim 3 PV1 (R5–6), wherein the poliovirus is PV1(M) and the IRES domains V and VI is substituted with the IRES domains V and VI of the Human Rhinovirus serotype 2.

12. A composition comprising a recombinant poliovirus according to claim 11 and a pharmaceutically acceptable carrier.

13. A recombinant poliovirus according to claim 3 PV1 (R6), wherein the poliovirus is PV1(M) and the IRES domain VI is substituted with the IRES domain VI of the Human Rhinovirus serotype 2.

14. A composition comprising a recombinant poliovirus according to claim 13 and a pharmaceutically acceptable carrier.

15. A recombinant poliovirus according to claim 3 PV1 (prr), wherein the poliovirus is PV1(M) and nt #484–nt #508 of the IRES domain V and nt #594–nt #612 of the IRES domain VI is substituted with nt #484–nt #508 of the IRES domain V and nt #594–nt #612 the IRES domain VI of the Human Rhinovirus serotype 2.

16. A composition comprising a recombinant poliovirus according to claim 15 and a pharmaceutically acceptable carrier.

17. A recombinant poliovirus according to claim 1 wherein, a part of the IRES, at least 19 nucleotides, of the poliovirus is substituted with a part of the IRES, at least 19 nucleotides, of the Human Rhinovirus serotype 1, 3–100.

18. A composition comprising a recombinant poliovirus according to claim 17 and a pharmaceutically acceptable carrier.

19. A recombinant poliovirus according to claim 1 wherein, a part of the IRES, at least 19 nucleotides, of the poliovirus is substituted with a part of the IRES, at least 19 nucleotides, of the Human Rhinovirus serotype 14.

20. A composition comprising a recombinant poliovirus according to claim 19 and a pharmaceutically acceptable carrier.

21. A recombinant poliovirus according to claim 1 wherein, a part of the IRES, at least 19 nucleotides, of the poliovirus is substituted with a part of the IRES, at least 19 nucleotides, of the coxsackievirus serotype B1 to B6.

22. A composition comprising a recombinant poliovirus according to claim 21 and a pharmaceutically acceptable carrier.

23. A recombinant poliovirus according to claim 21 wherein, a part of the IRES, at least 19 nucleotides, of the poliovirus is substituted with a part of the IRES, at least 19 nucleotides, of the coxsackievirus serotype B4.

24. A composition comprising a recombinant poliovirus according to claim 23 and a pharmaceutically acceptable carrier.

25. A recombinant poliovirus according to claim 1 wherein, a part of the IRES, at least 19 nucleotides, of the poliovirus is substituted with a part of the IRES, at least 19 nucleotides, of the human echovirus serotype 1 to 7, 9, 11 to 27, and 29 to 33.

26. A composition comprising a recombinant poliovirus according to claim 25 and a pharmaceutically acceptable carrier.

27. A recombinant poliovirus according to claim 25 wherein, a part of the IRES, at least 19 nucleotides, of the poliovirus is substituted with a part of the IRES, at least 19 nucleotides, of the human echovirus serotype 9.

28. A composition comprising a recombinant poliovirus according to claim 27 and a pharmaceutically acceptable carrier.

29. A composition according to any one of claims 2, 4, 6, 8, 10, 12, 14, 16, 18, 20, 22, 24, 26, or 28 or wherein the composition is infusible.

30. A composition according to any one of claims 2, 4, 6, 8, 10, 12, 14, 16, 18, 20, 22, 24, 26, or 28 wherein the composition is injectable.

31. A composition according to any one of claims 2, 4, 6, 8, 10, 12, 14, 16, 18, 20, 22, 24, 26, or 28 wherein the pharmaceutically acceptable carrier is a physiological salt solution.

32. A composition according to any one of claims 2, 4, 6, 8, 10, 12, 14, 16, 18, 20, 22, 24, 26, or 28 wherein the physiological salt solution is HANKS balanced salt solution.

* * * * *

SEQUENCE LISTING

```
(1) GENERAL INFORMATION:

(iii) NUMBER OF SEQUENCES:  28

(2) INFORMATION FOR SEQ ID NO:1:

(i) SEQUENCE CHARACTERISTICS:
          (A) LENGTH:  30
          (B) TYPE:  nucleotides
```

```
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Poliovirus
        (B) STRAIN:  Type 1 (Mahoney)

(viii) POSITION IN GENOME:
        (A) CHROMOSOME/SEGMENT:  IRES (xi) SEQUENCE DESCRIPTION: SEQ  ID. NO:1:
ccgaattcaa cttagaagtt tttcacaaag                                              30

(2) INFORMATION FOR SEQ ID NO:2:

(i) SEQUENCE CHARACTERISTICS:
        (A) LENGTH:  32
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Poliovirus
        (B) STRAIN:  Type 1 (Mahoney)

(viii) POSITION IN GENOME:
        (A) CHROMOSOME/SEGMENT:  IRES (xi) SEQUENCE DESCRIPTION: SEQ  ID. NO:2:
cctgagctcc catggtgcca atatatatat tg                                           32

(2) INFORMATION FOR SEQ ID NO:3:

(i) SEQUENCE CHARACTERISTICS:
        (A) LENGTH:  27
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Rhinovirus
        (B) STRAIN:  14

(viii) POSITION IN GENOME:
        (A) CHROMOSOME/SEGMENT:  IRES (xi) SEQUENCE DESCRIPTION: SEQ  ID. NO:3:
ccggaattcc cacccatgaa acgttag                                                 27

(2) INFORMATION FOR SEQ ID NO:4:

(i) SEQUENCE CHARACTERISTICS:
        (A) LENGTH:  26
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Rhinovirus
        (B) STRAIN:  14
```

(viii) POSITION IN GENOME:
              (A) CHROMOSOME/SEGMENT: IRES (xi) SEQUENCE DESCRIPTION: SEQ ID. NO:4:
cctgagctcc atgatcacag tatatg                                                  26

(2) INFORMATION FOR SEQ ID NO:5:

(i) SEQUENCE CHARACTERISTICS:
              (A) LENGTH: 36
              (B) TYPE: nucleotides
              (C) STRANDEDNESS: single
              (D) TOPOLOGY: linear (ii) MOLECULE TYPE: cDNA (iii) HYPOTHETICAL: No (vi) ORIGINAL SOURCE:
              (A) ORGANISM: Coxsackievirus
              (B) STRAIN: B4

(viii) POSITION IN GENOME:
              (A) CHROMOSOME/SEGMENT: IRES (xi) SEQUENCE DESCRIPTION: SEQ ID. NO:5:
cttagaattc aaagaaacaa tggtcaatta ctgacg                                        36

(2) INFORMATION FOR SEQ ID NO:6:

(i) SEQUENCE CHARACTERISTICS:
              (A) LENGTH: 20
              (B) TYPE: nucleotides
              (C) STRANDEDNESS: single
              (D) TOPOLOGY: linear (ii) MOLECULE TYPE: cDNA (iii) HYPOTHETICAL: No (vi) ORIGINAL SOURCE:
              (A) ORGANISM: Coxsackievirus
              (B) STRAIN: B4

(viii) POSITION IN GENOME:
              (A) CHROMOSOME/SEGMENT: IRES (xi) SEQUENCE DESCRIPTION: SEQ ID. NO:6:
cctgagctcc cattttatcg                                                          20

(2) INFORMATION FOR SEQ ID NO:7:

(i) SEQUENCE CHARACTERISTICS:
              (A) LENGTH: 27
              (B) TYPE: nucleotides
              (C) STRANDEDNESS: single
              (D) TOPOLOGY: linear (ii) MOLECULE TYPE: cDNA (iii) HYPOTHETICAL: No (vi) ORIGINAL SOURCE:
              (A) ORGANISM: Human Echovirus
              (B) STRAIN: serotype 9

(viii) POSITION IN GENOME:
              (A) CHROMOSOME/SEGMENT: IRES (xi) SEQUENCE DESCRIPTION: SEQ ID. NO:7:
ccgaattcag aagcatgact ccaacgg                                                  27

(2) INFORMATION FOR SEQ ID NO:8:

```
    (i) SEQUENCE CHARACTERISTICS:
        (A) LENGTH:  32
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Echovirus
        (B) STRAIN:  serotype 9

(viii) POSITION IN GENOME:
        (A) CHROMOSOME/SEGMENT:  IRES (xi) SEQUENCE DESCRIPTION: SEQ  ID. NO:8:
gggagctccc attttgatgt attgagtgtt aa                                   32

(2) INFORMATION FOR SEQ ID NO:9:

(i) SEQUENCE CHARACTERISTICS:
        (A) LENGTH:  22
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Poliovirus
        (B) STRAIN:  Type 1 (Mahoney)

(viii) POSITION IN GENOME:
        (A) CHROMOSOME/SEGMENT:  P1

(xi) SEQUENCE DESCRIPTION: SEQ  ID. NO:9:
ccgagctcag gtttcatcac ag                                              22

(2) INFORMATION FOR SEQ ID NO:10:

(i) SEQUENCE CHARACTERISTICS:
        (A) LENGTH:  22
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Poliovirus
        (B) STRAIN:  Type 1 (Mahoney)

(viii) POSITION IN GENOME:
        (A) CHROMOSOME/SEGMENT:  P1

(xi) SEQUENCE DESCRIPTION: SEQ  ID. NO:10:
ccgagctcag gtttcatcac ag                                              22

(2) INFORMATION FOR SEQ ID NO:11:

(i) SEQUENCE CHARACTERISTICS:
        (A) LENGTH:  29
        (B) TYPE:  nucleotides
        (C) STRANDEDNESS:  single
        (D) TOPOLOGY:  linear (ii) MOLECULE TYPE:  cDNA (iii) HYPOTHETICAL: No
```

```
      (vi) ORIGINAL SOURCE:
           (A) ORGANISM:  Poliovirus
           (B) STRAIN:  Type 1 (Mahoney)

(viii) POSITION IN GENOME:
           (A) CHROMOSOME/SEGMENT:  P3

(xi) SEQUENCE DESCRIPTION: SEQ  ID. NO:11:
ggagatcttg gatgccaaag cgctcgaag                                      29

(2) INFORMATION FOR SEQ ID NO:12:

(i) SEQUENCE CHARACTERISTICS:
           (A) LENGTH:  25
           (B) TYPE:  nucleotides
           (C) STRANDEDNESS:  single
           (D) TOPOLOGY:  linear (ii) MOLECULE TYPE:  cDNA (iii) HYPOTHETICAL: No (vi) ORIGINAL SOURCE:
           (A) ORGANISM:  Poliovirus
           (B) STRAIN:  Type 1 (Mahoney)

(viii) POSITION IN GENOME:
           (A) CHROMOSOME/SEGMENT:  P3

(xi) SEQUENCE DESCRIPTION: SEQ  ID. NO:12:
ggctcgagct tggttttgga cgggg                                          25

(2) INFORMATION FOR SEQ ID NO:13:

(i) SEQUENCE CHARACTERISTICS:
           (A) LENGTH:  39
           (B) TYPE:  nucleotides
           (C) STRANDEDNESS:  single
           (D) TOPOLOGY:  linear (ii) MOLECULE TYPE:  cDNA (iii) HYPOTHETICAL: No (vi) ORIGINAL SOURCE:
           (A) ORGANISM:  Poliovirus
           (B) STRAIN:  Type 1 (Sabin)

(viii) POSITION IN GENOME:
           (A) CHROMOSOME/SEGMENT:  P3

(xi) SEQUENCE DESCRIPTION: SEQ  ID. NO:13:
ggctcgagcc cagtgctttc cactatgtgt ttgaagggg                           39

(2) INFORMATION FOR SEQ ID NO:14:

(i) SEQUENCE CHARACTERISTICS:
           (A) LENGTH:  29
           (B) TYPE:  nucleotides
           (C) STRANDEDNESS:  single
           (D) TOPOLOGY:  linear (ii) MOLECULE TYPE:  cDNA (iii) HYPOTHETICAL: No (vi) ORIGINAL SOURCE:
           (A) ORGANISM:  Poliovirus
           (B) STRAIN:  Type 1 (Sabin)

(viii) POSITION IN GENOME:
           (A) CHROMOSOME/SEGMENT:  P3

(xi) SEQUENCE DESCRIPTION: SEQ  ID. NO:14:
tccggaagca ataaagctct tccaattgg                                      29
```

(2) INFORMATION FOR SEQ ID NO:15:

(i) SEQUENCE CHARACTERISTICS:
        (A) LENGTH:  53
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Poliovirus
        (B) STRAIN:  Type 1 (Sabin)

(viii) POSITION IN GENOME:
        (A) CHROMOSOME/SEGMENT:  3'NTR (xi) SEQUENCE DESCRIPTION: SEQ ID. NO:15:
gtccggagta ctcaacattg taccgccgtt ggcttgactc 40
attttagtaa ccc 53

(2) INFORMATION FOR SEQ ID NO:16:

(i) SEQUENCE CHARACTERISTICS:
(A) LENGTH: 26
(B) TYPE: nucleotides
(C) STRANDEDNESS: single
(D) TOPOLOGY: linear (ii) MOLECULE TYPE: cDNA (iii) HYPOTHETICAL: No (vi) ORIGINAL SOURCE:
(A) ORGANISM: Poliovirus
(B) STRAIN: Type 1 (Sabin)

(viii) POSITION IN GENOME:
(A) CHROMOSOME/SEGMENT: 3'NTR (xi) SEQUENCE DESCRIPTION: SEQ ID. NO:16:
ggtgcgaacg ttgttgccat tgctgc 26

(2) INFORMATION FOR SEQ ID NO:17:

(i) SEQUENCE CHARACTERISTICS:
(A) LENGTH: 26
(B) TYPE: nucleotides
(C) STRANDEDNESS: single
(D) TOPOLOGY: linear (ii) MOLECULE TYPE: cDNA (iii) HYPOTHETICAL: No (vi) ORIGINAL SOURCE:
(A) ORGANISM: Human Rhinovirus
(B) STRAIN: Type 2

(viii) POSITION IN GENOME:
(A) CHROMOSOME/SEGMENT: IRES (xi) SEQUENCE DESCRIPTION: SEQ ID. NO:17:
ccggatccaa agcgagcaca cggggc 26

(2) INFORMATION FOR SEQ ID NO:18:

(i) SEQUENCE CHARACTERISTICS:
(A) LENGTH: 25
(B) TYPE: nucleotides
(C) STRANDEDNESS: single
(D) TOPOLOGY: linear

```
        (ii) MOLECULE TYPE: cDNA (iii) HYPOTHETICAL: No (vi) ORIGINAL SOURCE:
             (A) ORGANISM: Poliovirus
             (B) STRAIN: Type 1 (Mahoney)

(viii) POSITION IN GENOME:
             (A) CHROMOSOME/SEGMENT: IRES (xi) SEQUENCE DESCRIPTION: SEQ ID. NO:18:
ccggatcctc cggcccctga atgcg                                              25

(2) INFORMATION FOR SEQ ID NO:19:

(i) SEQUENCE CHARACTERISTICS:
             (A) LENGTH: 30
             (B) TYPE: nucleotides
             (C) STRANDEDNESS: single
             (D) TOPOLOGY: linear (ii) MOLECULE TYPE: cDNA (iii) HYPOTHETICAL: No (vi) ORIGINAL SOURCE:
             (A) ORGANISM: Poliovirus
             (B) STRAIN: Type 1 (Mahoney)

(viii) POSITION IN GENOME:
             (A) CHROMOSOME/SEGMENT: IRES (xi) SEQUENCE DESCRIPTION: SEQ ID. NO:19:
cctgagctcc cattatgata caattgtctg                                         30

(2) INFORMATION FOR SEQ ID NO:20:

(i) SEQUENCE CHARACTERISTICS:
             (A) LENGTH: 33
             (B) TYPE: nucleotides
             (C) STRANDEDNESS: single
             (D) TOPOLOGY: linear (ii) MOLECULE TYPE: cDNA (iii) HYPOTHETICAL: No (vi) ORIGINAL SOURCE:
             (A) ORGANISM: Human Rhinovirus
             (B) STRAIN: Type 2

(viii) POSITION IN GENOME:
             (A) CHROMOSOME/SEGMENT: IRES (xi) SEQUENCE DESCRIPTION: SEQ ID. NO:20:
ggtaccaata aaataaaagg aaacacggac acc                                     33

(2) INFORMATION FOR SEQ ID NO:21:

(i) SEQUENCE CHARACTERISTICS:
             (A) LENGTH: 29
             (B) TYPE: nucleotides
             (C) STRANDEDNESS: single
             (D) TOPOLOGY: linear (ii) MOLECULE TYPE: cDNA (iii) HYPOTHETICAL: No (vi) ORIGINAL SOURCE:
             (A) ORGANISM: Human Rhinovirus
             (B) STRAIN: Type 2

(viii) POSITION IN GENOME:
```

(A) CHROMOSOME/SEGMENT:  IRES (xi) SEQUENCE DESCRIPTION: SEQ   ID. NO:21:
gcggtaccgc ttatggtgac aatatatac                                              29

(2) INFORMATION FOR SEQ ID NO:22:

(i) SEQUENCE CHARACTERISTICS:
        (A) LENGTH:  27
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Rhinovirus
        (B) STRAIN:  Type 2

(viii) POSITION IN GENOME:
        (A) CHROMOSOME/SEGMENT:  IRES (xi) SEQUENCE DESCRIPTION: SEQ   ID. NO:22:
ccggtaccta aaggaaaaag tgaaaca                                                27

(2) INFORMATION FOR SEQ ID NO:23:

(i) SEQUENCE CHARACTERISTICS:
        (A) LENGTH:  28
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Echovirus
        (B) STRAIN:  serotype 9

(viii) POSITION IN GENOME:
        (A) CHROMOSOME/SEGMENT:  IRES (xi) SEQUENCE DESCRIPTION: SEQ   ID. NO:23:
ccggtaccgc ttatggtgac aatcacag                                               28

(2) INFORMATION FOR SEQ ID NO:24:

(i) SEQUENCE CHARACTERISTICS:
        (A) LENGTH:  25
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Echovirus
        (B) STRAIN:  serotype 9

(viii) POSITION IN GENOME:
        (A) CHROMOSOME/SEGMENT:  IRES (xi) SEQUENCE DESCRIPTION: SEQ   ID. NO:24:
gggaattcag acgcacaaaa ccaag                                                  25

(2) INFORMATION FOR SEQ ID NO:25:

(i) SEQUENCE CHARACTERISTICS:
        (A) LENGTH:  25

```
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Rhinovirus
        (B) STRAIN:  Type 2

(viii) POSITION IN GENOME:
        (A) CHROMOSOME/SEGMENT:  IRES (xi) SEQUENCE DESCRIPTION: SEQ  ID. NO:25:
ccggatcctt atgtagctca atagg                                            25

(2) INFORMATION FOR SEQ ID NO:26:

(i) SEQUENCE CHARACTERISTICS:
        (A) LENGTH:  25
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Rhinovirus
        (B) STRAIN:  Type 2

(viii) POSITION IN GENOME:
        (A) CHROMOSOME/SEGMENT:  IRES (xi) SEQUENCE DESCRIPTION: SEQ  ID. NO:26:
ccggatcctt atgtagctca atagg                                            25

(2) INFORMATION FOR SEQ ID NO:27:

(i) SEQUENCE CHARACTERISTICS:
        (A) LENGTH:  28
        (B) TYPE:  nucleotides
        (C) STRANDEDNESS:  single
        (D) TOPOLOGY:  linear (ii) MOLECULE TYPE:  cDNA (iii) HYPOTHETICAL: No (vi) ORIGINAL SOURCE:
        (A) ORGANISM:  Human Rhinovirus
        (B) STRAIN:  Type 2

(viii) POSITION IN GENOME:
        (A) CHROMOSOME/SEGMENT:  IRES (xi) SEQUENCE DESCRIPTION: SEQ  ID. NO:27:
ggttacgtgc tctagctccg aggttggg                                         28

(2) INFORMATION FOR SEQ ID NO:28:

(i) SEQUENCE CHARACTERISTICS:
        (A) LENGTH:  44
        (B) TYPE:  nucleotides
        (C) STRANDEDNESS:  single
        (D) TOPOLOGY:  linear (ii) MOLECULE TYPE:  cDNA (iii) HYPOTHETICAL: No
```

```
    (vi) ORIGINAL SOURCE:
         (A) ORGANISM:  Human Rhinovirus
         (B) STRAIN:  Type 2

(viii) POSITION IN GENOME:
         (A) CHROMOSOME/SEGMENT:  IRES (xi) SEQUENCE DESCRIPTION: SEQ  ID. NO:28:
agagcacgta acccaatgtg tatctagtcg taacgcgcaa                         40
ctcc                                                                44
```